United States Patent
Timmerman et al.

[11] Patent Number: 6,127,360
[45] Date of Patent: Oct. 3, 2000

[54] DIAMINE DERIVATIVES AND PHARMACEUTICAL CONTAINING THE SAME

[75] Inventors: Henk Timmerman, Voorschoten, Netherlands; Minggiang Zang, Scotland, United Kingdom; Kazuhiro Onogi, Iruma, Japan; Masahiro Tamura; Tsutomu Tohma, both of Higashimurayama, Japan; Yasushi Wada, Tachikawa, Japan

[73] Assignee: Kowa Co., Ltd., Nagoya, Japan

[21] Appl. No.: 09/147,777

[22] PCT Filed: Jul. 7, 1998

[86] PCT No.: PCT/JP98/03054

§ 371 Date: Mar. 5, 1999

§ 102(e) Date: Mar. 5, 1999

[87] PCT Pub. No.: WO99/02520

PCT Pub. Date: Jan. 21, 1999

[30] Foreign Application Priority Data

Jul. 7, 1997 [JP] Japan ..................... 9-181196

[51] Int. Cl.[7] ............ C07D 279/16; C07D 239/72; C07D 401/00; C07D 403/00
[52] U.S. Cl. ........................................ 514/211.05
[58] Field of Search ................... 540/575, 203, 540/461, 523; 544/363, 370, 49, 283, 52; 514/210, 213, 218, 252, 224.2, 253, 210.04, 211.05, 211.08, 253.01, 252.17, 252.13, 253.06, 253.07, 253.09, 253.1, 254.01, 254.05, 254.09

[56] References Cited

FOREIGN PATENT DOCUMENTS

| 905133 | 3/1999 | European Pat. Off. . |
| 7-149646 | 6/1995 | Japan . |
| 9-227561 | 9/1997 | Japan . |
| 9-59158 | 3/1998 | Japan . |

*Primary Examiner*—Mukund J. Shah
*Assistant Examiner*—Ben Schroeder
*Attorney, Agent, or Firm*—Oblon, Spivak, McClelland, Maier & Neustadt, P.C.

[57] ABSTRACT

This invention relates to a diamine derivative represented by the following formula (1) or a salt thereof.

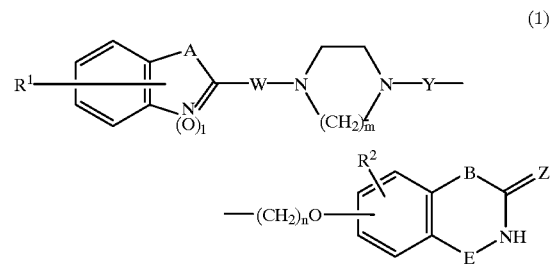

wherein $R^1$ represents H, OH, an aralkyloxy group or a halogen atom; $R^2$ represents H or a lower alkyl group; A represents —C($R^3$)=CH—, —CH=N—, —N($R^4$)—, $R^3$ being H or OH, $R^4$ being a lower alkyl group or an alkoxyalkyl group, —O—, or —S—; B represents a single bond, —C($R^5$)($R^6$)—($CH_2$)$_k$—, $R^5$ and $R^6$ being H or a lower alkyl group, and k being a value of from 0 to 2, —S(O)$_q$CH($R^7$), or —CH=CH—; E represents a single bond or —($CH_2$)$_3$—; W and Y individually represent —$CH_2$— or —CO—; Z represents O or S; and m is a value of 2 or 3, and n is a value of from 1 to 4; with the proviso that E is —($CH_2$)$_3$— when B is a single bond and E is a single bond when B is a group other than a single bond. The diamine derivatives or salts thereof have both antileukotrienic action and antihistaminic action and are low in brain penetration, and are hence useful as asthma preventives and curatives.

7 Claims, No Drawings

DIAMINE DERIVATIVES AND PHARMACEUTICAL CONTAINING THE SAME

TECHNICAL FIELD

This invention relates to novel diamine derivatives having antihistaminic action and antileukotrienic action and also to medicines containing the same.

BACKGROUND ART

Histamine exhibits bronchial smooth muscle constricting action and capillaropenetration accelerating action as a result of its binding to the $H_1$ receptor in cell membranes, and is considered to be an important mediator in allergic diseases. Described specifically, histamine is believed to cause aggravation of asthmatic symptoms by its bronchoconstricting action and also to increase transudation of blood components into intercellular spacings due to accelerated capillaropenetration and hence to take part in the formation of edema seen in allergic rhinitis and conjunctivitis. For the treatment of these allergic diseases, antihistaminic agents are therefore used. Conventional antihistaminic agents however bind to the $H_1$ receptor in the brain, so that side effects on the central nerve system, such as drowsiness, are concerned. In recent years, bronchial asthma is regarded as eosinophilic chronic inflammation of the airway, and a late asthmatic response that the symptom of airway constriction which is typical to asthma is developed due to infiltration of inflammatory cells on the bronchial mucosa, oversecretion of mucus and the like is at issue. Antihistaminic agents are not effective for such late asthmatic responses, leading to the existence of an outstanding desire for the development of pharmaceuticals of a new type for their treatment.

Leukotrienes (LT) are associated with causes for most inflammatory diseases, especially asthma, psoriasis, rheumatism and inflammatory colitis, and are considered to play an important role in inflammatory processes through cytopathy. Leukotrienes are principal mediators of allergy and inflammation, and therefore many substances which inhibit the action and/or syntheses of leukotrienes are being discovered for the treatment of these diseases (S. T. Holgate et al.: J. Allergy Clin. Immunol., 98, 1–13, 1996).

Leukotrienes are arachidonate metabolites synthesized by 5-lipoxygenase (5-LO), and consist of two groups. One of the groups is $LTB_4$ and has strong chemotaxis towards leukocytes. The other group is collectively called cysteine leukotrienes (CySLT) and includes $LTC_4$, $LTD_4$ and $LTE_4$. As biologically active substances, they have been called "slow-reacting substances of anaphylaxis (SRS-A)" for many years. CysLT binds to their receptors in human tissues to exert its action. A selective $LTD_4$ receptor inhibitor has been found to inhibit contracting actions of both $LTC_4$ and $LTD_4$ in human lung tissues, so that $LTC_4$ is suggested to bind to the same site of a receptor as $LTD_4$ (Buckner C. K. et al: Ann. NY Acad. Sci., 524, 181–6, 1988; Aharony D. et al.: New Trends in Lipid Mediators Research, Basel: Karger 67–71, 1989). $LTE_4$ is also considered to act via the same receptor as $LTD_4$, but is called a partially active substance for its lower potency.

Described specifically, in an allergic disease such as asthma, an immediate asthmatic response such as bronchial constriction and edematous formation, in which histamine or the like takes principal part, and a late asthmatic response such as airway constriction due to cell infiltration, mucus secretion or mucosal hypertrophy, in which a leukotriene or the like takes part are considered to be important for the development of morbid conditions. In allergic rhinitis, there is similarly a move toward taking each morbid condition as a biphasic response that histamine takes a profound part in an immediate response such as sternutation or nasal oversecretion and leukotriene takes an important part in a late response such as a rhinostenostic symptom due to edema of the nasal mucosa.

A compound having antagonism against both a histamine $H_1$ receptor and an $LTD_4$ receptor and less tendency of brain penetration is therefore considered to prevent or cure a variety of allergic diseases, especially a series of symptoms of asthma or rhinitis, which ranges from an immediate response to a late response, and to become an effective pharmaceutical of reduced side effects.

It is however the current circumstances that no compound has been found with fully satisfactory antagonism against both an $LTD_4$ receptor and a histamine $H_1$ receptor. Further, many of $LTD_4$ antagonists which have been developed so far contain at least one acidic group, so that these $LTD_4$ antagonists are hydrophilic compounds having high polarity. They are thus unavoidably insufficient in absorption upon inhalative administration or oral administration. This is believed to have led to the increased doses of these pharmaceuticals and hence, to the development of side effects.

Therefore, an object of the present invention is to provide a compound making combined use of both antileukotrienic action and antihistaminic action, having low tendency of brain penetration and containing no acidic group in its molecule; and also a medicine comprising this compound as an effective ingredient.

DISCLOSURE OF THE INVENTION

With the foregoing current circumstances in view, the present inventors have conducted an extensive investigation. As a result, it has been found that novel diamine derivatives represented by the following formula (1) and salts thereof meet the above-described requirements, leading to the completion of the present invention.

Specifically, the present invention provides a diamine derivative represented by the following formula (1) or a salt thereof:

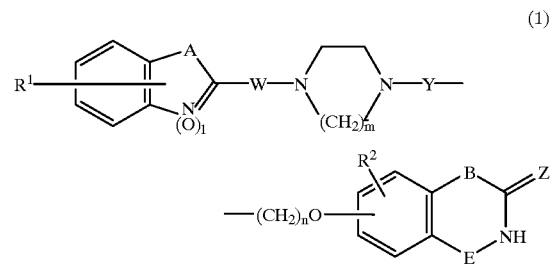

wherein $R^1$ represents a hydrogen atom, a hydroxyl group, an aralkyloxy group or a halogen atom;

$R^2$ represents a hydrogen atom or a lower alkyl group;

A represents —C($R^3$)=CH—, $R^3$ being a hydrogen atom or a hydroxyl group, —CH=N—, —N($R^4$)—, being a lower alkyl group or an alkoxyalkyl group, —O—, or —S—;

B represents a single bond, —C($R^5$)($R^6$)—(CH$_2$)$_k$—, $R^5$ and $R^6$ being the same or different and individually representing a hydrogen atom or a lower alkyl group, and k being a value of from 0 to 2, —S(O)$_q$CH($R^7$), q being a value of from 0 to 2, and $R^7$ being a hydrogen atom or a hydroxyl group, or —CH═CH—;

E represents a single bond or —(CH$_2$)$_3$—;

W and Y may be the same or different and individually represent —CH$_2$— or —CO—;

Z represents an oxygen atom or a sulfur atom; and l is a value of 0 or 1, m is a value of 2 or 3, and n is a value of from 1 to 4; with the proviso that E is —(CH$_2$)$_3$ when B is a single bond and E is a single bond when B is a group other than a single bond.

Further, the present invention also provides a medicine comprising as an effective ingredient a diamine derivative represented by the formula (1) or a salt thereof.

In addition, the present invention also provides a medicinal composition comprising a diamine derivative represented by the formula (1) or a salt thereof and a pharmaceutically acceptable carrier.

Furthermore, the present invention also provides use of a diamine derivative represented by the formula (1) or a salt thereof as a medicine.

Moreover, the present invention also provides a method for treating an allergic disease, which comprises administering an effective amount of a diamine derivative represented by the formula (1) or a salt thereof.

BEST MODES FOR CARRYING OUT THE INVENTION

In the formula (1), examples of the halogen atom represented by $R^1$ include fluorine, chlorine, bromine and iodine atoms. Examples of the aralkyloxy group include phenylalkyloxy groups, preferably phenyl-C$_1$–C$_6$ alkyloxy groups, notably a benzyloxy group. As $R^1$, a hydrogen atom or a hydroxyl group is preferred.

Illustrative of the lower alkyl groups represented by $R^2$, $R^4$, $R^5$ and $R^6$ are linear or branched alkyl groups having 1–6 carbon atoms, for example, methyl, ethyl, n-propyl, isopropyl, n-butyl, isobutyl, t-butyl, n-pentyl and n-hexyl, with methyl being particularly preferred.

Illustrative of the alkoxyalkyl group represented by $R^4$ are C$_{1-6}$ alkyl groups substituted by C$_{1-6}$ alkoxy groups, for example, methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl and propoxybutyl, with ethoxyethyl being particularly preferred.

In the formula (1), examples of

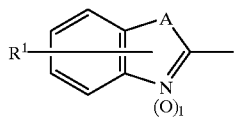

include the following groups:

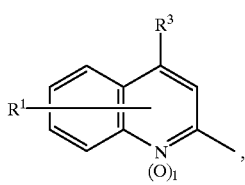 , 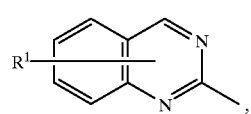 ,

-continued

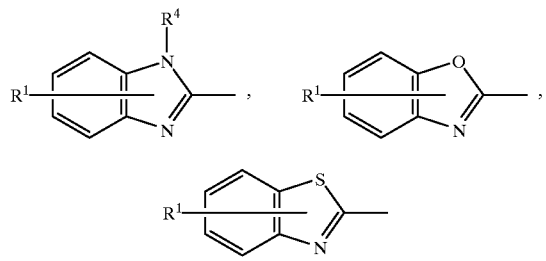

Further, examples of in

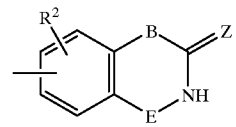

in the formula (1) include the following groups:

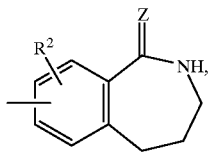 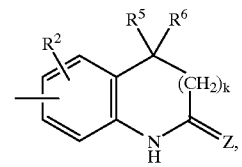

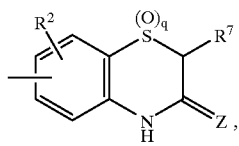 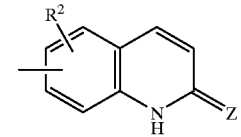

wherein $R^1$, $R^2$, $R^3$, $R^4$, $R^5$, $R^6$, $R^7$, Z, l, k and q have the same meanings as defined above.

No particular limitation is imposed on the salt of the diamine derivative (1) of the present invention, insofar as it is a pharmacologically acceptable salt. Illustrative are mineral acid addition salts such as the hydrochloride, hydrobromide, hydroiodide, sulfate and phosphate; and organic acid addition salts such as the benzoate, methanesulfonate, ethanesulfonate, benzenesulfonate, p-toluenesulfonate, oxalate, maleate, fumarate, tartrate and citrate.

Further, the compound of the present invention may also exist in the form of solvates, which are typified by the hydrate, or a keto-enol tautomer. Such solvates and isomer are also included in the present invention.

The compound (1) of the present invention can be prepared, for example, in accordance with the following reaction process.

Process A

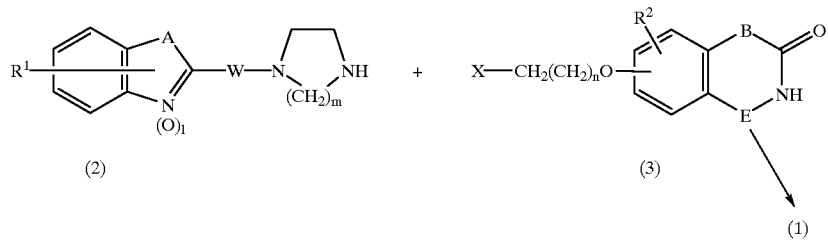

(2)        (3)

(1)

Process B

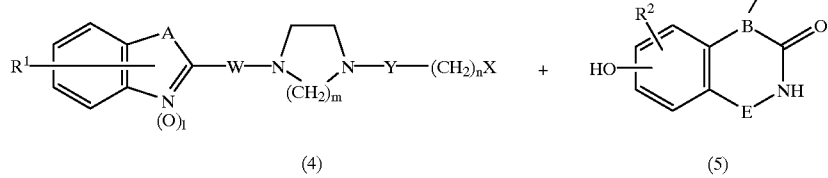

(4)        (5)

wherein A, B, E, $R^1$, $R^2$, W, Y, Z, l, m and n have the same meanings as defined above, and X represents a chlorine atom, bromine atom or iodine atom.

Described specifically, a compound (1) of the present invention in which Y is —$CH_2$— can be prepared by reacting a diamine compound (2) with a haloalkylated phenol compound (3) as shown by the process A or by reacting a haloalkylated diamine compound (4) with a phenol compound (5) as shown by the process B. A compound (1) of the present invention in which Y is —CO— can be prepared by reacting a haloacylated diamine compound (4) with a phenol compound (5) as shown by the process B.

The above reactions can each be practiced by conducting heating for 1 to 24 hours (preferably at 100 to 200° C.) under an inert gas stream in a solventless manner or in an aprotic solvent such as acetone, 2-butanone, dimethylformamide (DMF), dimethylsulfoxide (DMSO) or hexamethylphosphoroamide (HMPA). Upon practice, an inorganic base such as potassium carbonate and an inorganic salt such as potassium iodide may be added.

Further, a compound (1) of the present invention in which $R^1$ is a hydroxyl group can be obtained by subjecting a compound (1) of the present invention, in which $R^1$ is an aralkyloxy group, to a catalytic hydrogenating reaction in the presence of a catalyst such as palladium on charcoal or in a manner known per se in the art.

A description will next be made about synthesis processes of the compounds (2) to (5) useful in the above reactions.

The diamine compound (2) for use in the process A can be prepared by a known process, for example, the process disclosed in Pesson, Marcel et al.: Eur. J. Med. Chem.-Chim. Ther., 10(6), 567–572, 1975; Imura, Ryuichi et al.: J. Heterocycl. Chem., 24, 31–37, 1987; Meyer, Walter E. et al.: J. Med. Chem., 32(3), 593–597, 1989; or the like, or in accordance with the reaction scheme shown below.

Process C

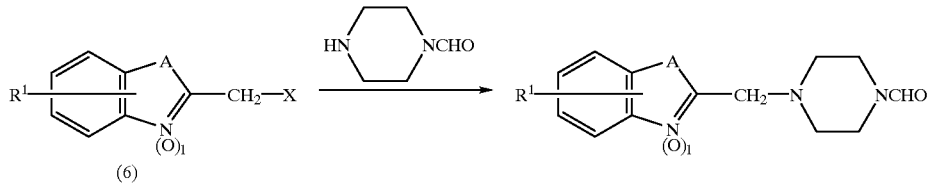

(6)                     (7)

Process D

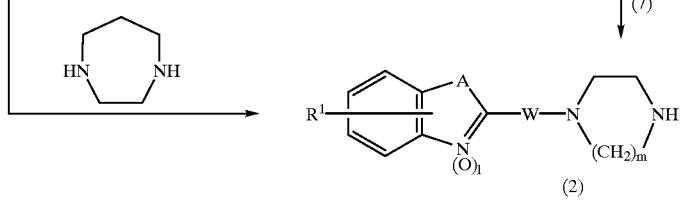

(2)

-continued

Process E

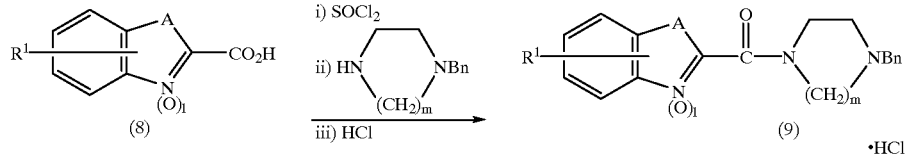

wherein A, R$^1$, W, l and m have the same meanings as defined above, Bn represents a benzyl group, and X represents a chlorine atom, bromine atom or iodine atom.

Described specifically, a compound (2) in which W is —CH$_2$— and m is 2 can be obtained, as shown by the process C, by reacting a halomethyl derivative (6) and N-formylpiperazine in the presence of a base such as pyridine or triethylamine in a polar solvent such as methanol or ethanol at 0° C. to reflux temperature (preferably room temperature) for 1 to 7 days to obtain a compound (7) and then reacting and deformylating the compound (7) in a polar solvent such as methanol or ethanol in the presence of an acid, such as concentrated sulfuric acid, added therein at 0° C. to reflux temperature (preferably reflux temperature) for 1 to 4 days.

A compound (2) in which W is —CH$_2$— and m is 3 can be obtained, as shown by the process D, by reacting a halomethyl derivative (6) and homopiperazine in the presence of a base such as triethylamine in a polar solvent such as methanol or ethanol at 0° C. to reflux temperature (preferably room temperature) for 1 to 7 days.

Further, a compound (2) in which W is —CO— can be obtained, as shown by the process E, by chlorinating a carboxylic acid (8) with thionyl chloride or the like, reacting the chlorinated product with N-benzyl-piperazine or N-benzylhomopiperazine to obtain a compound (9), reducingly debenzylating the compound (9), for example, with a palladium-charcoal catalyst or the like under a hydrogen gas stream, and then converting the resulting hydrochloride of the compound (2) into a free base.

The haloalkylated phenol compound (3) useful in the process A can be obtained, as shown below, by reacting the phenol compound (10) and a dihalogenide of a linear alkane in an aprotic solvent such as acetone, 2-butanone, DMF, DMSO or HMPA at 0° C. to reflux temperature (preferably reflux temperature) for 1 to 24 hours.

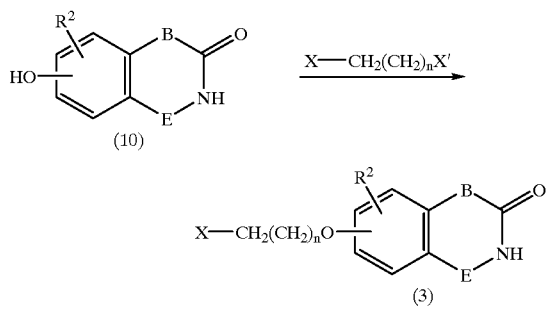

wherein B, E, R$^2$ and n have the same meanings as defined above, and X and X' may be the same or different and individually represent a chlorine atom, bromine atom or iodine atom.

Among diamine compounds (4) useful in the process B, each compound (4a) in which Y is —CH$_2$— can be obtained, as shown below, by reacting a compound (2) and a dihalogenide of a linear alkane in an aprotic solvent such as acetone, 2-butanone, DMF, DMSO or HMPA at 0° C. to reflux temperature (preferably reflux temperature) for 1 to 24 hours.

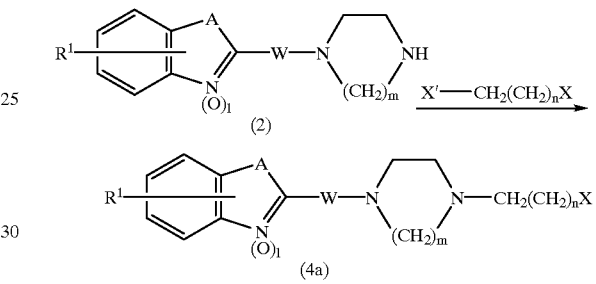

wherein A, R$^1$, W, l, m and n have the same meanings as defined above, and X and X' may be the same or different and individually represent a chlorine atom, bromine atom or iodine atom.

Among the diamine compounds (4) useful in the process B, each compound (4b) in which Y is —CO— can be obtained by haloacylating a compound (2) by a method known per se in the art as shown below.

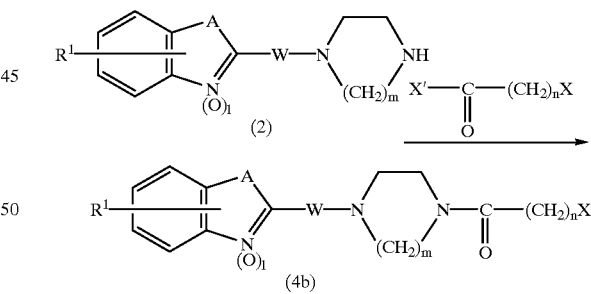

wherein A, R$^1$, W, l, m and n have the same meanings as defined above, and X and X' may be the same or different and individually represent a chlorine atom, bromine atom or iodine atom.

Incidentally, as the compound (5), compound (6), compound (8) and compound (10), either conventionally known compounds or those prepared by conventionally known processes, for example, by the processes disclosed in Musser, John H. et al.: J. Med. Chem., 33(1), 240–245, 1990; Iemura, Ryuichi et al.: J. Heterocyclic Chem., 24(1), 31–37, 1987; Jaromin Gunter E. et al.: Chem. Ber. 120, 649–651, 1987; White, James D. et al.: J. O. C. 58, 3466–3468, 1993; etc. can be used.

The compound (1) of the present invention can be obtained by treating the reaction mixture by a method known per se in the art subsequent to the reaction by the process A or B. If necessary, it can be purified using a conventional purification method such as recrystallization or column chromatography. By a method known per se in the art, it can be converted into a desired salt as needed.

As will be demonstrated subsequently in Examples, the invention compound (1) or salt thereof available as described above has excellent antileukotrienic action and antihistaminic action in combination, has lower tendency of penetration to the center than terfenadine, and is useful as a medicine for asthma, allergic rhinitis, allergic dermatitis, allergic conjunctivitis, urticaria and psoriasis.

The medicine according to the present invention comprises the above-described compound (1) or a salt or solvate thereof as an effective ingredient. It is however preferred to use it as a medicinal composition which comprises the effective ingredient and a pharmaceutically acceptable carrier. Its administration forms as such medicinal compositions include, for example, oral administration forms such as tablets, capsules, granules, powders and syrups; and parenteral administration forms such as intravenous injections, intramuscular injections, suppositories, inhalative agents, percutaneous absorption agents, eye drops and nasal drops. Upon production of medicinal preparations in such various administration forms, the effective ingredient can be used either singly or by suitably combining the same with one or more pharmaceutically acceptable carriers such as excipients, binders, extenders, disintegrants, surfactants, lubricants, dispersants, buffers, preservatives, corrigents, perfumes, coating materials, diluents and the like.

The dosage of the medicine according to the present invention varies depending on the age, body weight, conditions, administration form, administration frequency and the like. In general, however, it is preferred to orally or parenterally administer to an adult the compound (1) or its salt or solvate in an amount of about 1 to 1,000 mg per day at once or in several portions.

EXAMPLES

The present invention will next be described in further detail by the following Examples. It should however be borne in mind that the present invention is by no means limited to these Examples.

Preparation Example 1

Synthesis of 1-formyl-4-(2-guinolylmethyl)piperazine

After a mixture consisting of 2-chloromethyl-quinoline hydrochloride (85.64 g, 400 mmol), triethyl-amine (80.95 g, 800 mmol), N-formylpiperazine (45.66 g, 400 mmol) and ethanol (900 ml) was stirred at room temperature for 7 days, the solvent was distilled off under reduced pressure. The resultant residue was dissolved in water, washed with ethyl ether, and then extracted with chloroform. The extract was washed with water and dried over anhydrous magnesium sulfate. The solvent was distilled off under reduced pressure, whereby 86.00 g the title compound were obtained as a pale yellow oil (yield: 82.9%).

$^1$H-NMR(CDCl$_3$)δ(ppm): 8.16(1H,d,J=8.3 Hz), 8.09(1H, d,J=8.3 Hz), 8.06(1H,s), 7.88–7.45(4H,m), 3.88(2H,s), 3.66–3.50(2H,m), 3.48–3.32(2H,m), 2.64–2.45(4H,m).

IR(film)cm$^{-1}$: 2817, 1665, 1443, 1140, 1018, 1005, 838, 827, 786, 758.

Preparation Example 2

Synthesis of 1-(2-quinolylmethyl)piperazine

1-Formyl-4-(2-quinolylmethyl)piperazine (86.00 g, 332 mmol) was dissolved in ethanol (800 ml), followed by the addition of concentrated sulfuric acid (49.04 g, 500 mmol). After the resulting mixture was heated under reflux and stirring for 4 days, the solvent was distilled off under reduced pressure. The thus-obtained residue was dissolved in water. After the resulting solution was washed twice with chloroform, the solution was rendered basic with a 10N aqueous solution of sodium hydroxide, followed by extraction with chloroform. The extract was washed with water and then dried over anhydrous magnesium sulfate. The solvent was distilled off under reduced pressure, whereby 73.65 g of the title compound were obtained as a pale amber oil (yield: 97.6%).

$^1$H-NMR(CDCl$_3$)δ(ppm): 8.13(1H,d,J=8.8 Hz), 8.08(1H, d,J=9.3 Hz), 7.86–7.56(3H,m), 7.51(1H,t,J=6.8 Hz), 3.82 (2H,s), 3.00–2.84(4H,m), 2.65–2.44(4H,m).

IR(film)cm$^{-1}$: 3287, 2939, 2814, 1600, 1504, 1425, 1142, 1131, 1119, 835, 785, 754.

Preparation Example 3

Synthesis of 1-(2-quinolylmethyl)homopiperazine

After a mixture consisting of 2-chloromethyl-quinoline hydrochloride (63.16 g, 295 mmol), triethyl-amine (29.85 g, 295 mmol), homopiperazine (50.08 g, 591 mmol) and ethanol (600 ml) was stirred at room temperature for 2 days, the solvent was distilled off under reduced pressure. Water was added to the residue. After the resulting mixture was washed three times with ethyl ether, sodium chloride was added to the water layer, followed by extraction four times with chloroform-methanol (2:1). The extract was washed with an aqueous solution of sodium chloride and then dried over anhydrous magnesium sulfate. The solvent was distilled off under reduced pressure, whereby 28.00 g of the title compound were obtained as a yellow oil (yield: 39.3%).

$^1$H-NMR(CDCl$_3$)δ(ppm): 8.15(1H,d,J=8.8 Hz), 8.06(1H, d,J=8.3 Hz), 7.79(2H,d,J=7.8 Hz), 7.68(2H,d,J=8.8 Hz), 7.52(1H,t,J=6.8 Hz), 4.03(2H,s), 3.30–3.06(4H,m), 3.00–2.70(4H,m), 2.06–1.90(2H,m).

IR(film)cm$^{-1}$: 3100–2300, 1618, 1600, 1504, 1461, 1426, 1356, 1310, 1142, 1114, 1085, 1054, 834, 753.

Further, the ethyl ether washing was washed with water and then dried over anhydrous magnesium sulfate. The solvent was thereafter distilled off, whereby 18.15 g of 1,4-bis(2-quinolylmethyl)homopiperazine were obtained as a yellow oil (yield: 32.2%). A portion of the oil was crystallized from a mixed solvent of ethyl ether and n-hexane, whereby pale yellow prisms were obtained.

m.p.: 65–67° C. $^1$H-NMR(CDCl$_3$)δ(ppm): 8.13(2H,d,J= 8.8 Hz), 8.06(2H,d,J=8.8 Hz), 7.84–7.62(6H,m), 7.50(2H, td,J=8.3,1.5 Hz), 4.00(4H,s), 2.92–2.73(8H,m), 2.00–1.78 (2H,m).

IR(film)cm$^{-1}$: 3059, 2935, 2815, 1618, 1600, 1563, 1504, 1458, 1425, 1355, 1335, 1112, 833, 785, 757.

Preparation Examples 4–11

By similar processes as in Examples 1–3 or known processes, the compounds shown in Table 1 were obtained.

TABLE 1

| Prep. Ex. | Compound Name | Color, state of matter |
|---|---|---|
| 4 | 1-(2-Quinazolinylmethyl)piperazine | Amber oil |
| 5 | 1-(N-Methylbenzoimidazol-2-yl-methyl)piperazine | Amber oil |
| 6 | 1-(N-Methylbenzoimidazol-2-yl methyl)homopiperazine | Amber oil |
| 7 | 1-(N-Ethoxyethylbenzoimidazol-2-yl-methyl)piperazine | Amber oil |
| 8 | 1-(N-Ethoxyethylbenzoimidazo1-2-yl-methyl)homopiperazine | Amber oil |
| 9 | 1-(1-Oxo-2-quinolylmethyl)piperazine | Amber oil |
| 10 | 1-(8-Benzyloxy-2-quinolylmethyl)-piperazine | Colorless oil |
| 11 | 1-(4-Benzyloxy-2-quinolylmethyl)piperazine | Amber oil |

Preparation Example 12

Synthesis of 7-(3-chloropropoxy)-3,4-dihydro-2H-1,4-benzothiazin-3-one

After a mixture consisting of 7-hydroxy-3,4-dihydro-2H-1,4-benzothiazin-3-one (1.812 g, 10 mmol), 1bromo-3-chloropropane (2.362 g, 15 mmol), potassium carbate (4.146 g, 30 mmol) and acetone (40 mmol) was heated under reflux and stirring for 24 hours, insolube matter was filtered off, and the solvent was distilled off under reduced pressure. The residue was subjected to chromatography on a silica gel column (developer: chloroform) to purify the same, and was then recrystallized from acetone. The title compound (1.300 g) was obtained as yellow leaflets (yield: 50.4%).

m.p.: 150–152° C.

$^{1}$H-NMR(CDCl$_3$)δ(ppm): 8.80(1H,br.s), 6.87(1H,d,J=2.4 Hz), 6.82(1H,d,J=8.8 Hz), 6.73(1H,dd,J=8.3,2.4 Hz), 4.08 (2H,t,J=5.8 Hz), 3.74(2H,t,J=5.8 Hz), 3.42(2H,s), 2.32–2.14 (2H,m).

IR(KBr)cm$^{-1}$: 3262, 1671, 1635, 1502, 1468, 1387, 1243, 1233, 1033.

Preparation Examples 13–56

From known compounds or compounds available by known processes, the compounds shown in Tables 2 and 3 were obtained in a similar manner as in Preparation Example 12.

TABLE 2

| Prep. Ex. | Compound Name | Melting point (° C.) |
|---|---|---|
| 13 | 6-(3-Chloropropoxy)-2,3,4,5-tetrahydro-1H-1-benzoazepin-2-one | 110–112 |
| 14 | 7-(3-Chloropropoxy)-2,3,4,5-tetrahydro-1H-1-benzoazepin-2-one | 121–123 |
| 15 | 7-(3-Chloropropoxy)-2,3,4,5-tetrahydro-1H-2-benzoazepin-1-one | 132–133 |
| 16 | 7-(2-Chloroethoxy)-3,4-dihydro-2H-1,4-benzothiazin-3-one | 179–181 |
| 17 | 7-(4-Chlorobutoxy)-3,4-dihydro-2H-1,4-benzothiazin-3-one | 137–139 |
| 18 | 7-(5-Chloropentyloxy)-3,4-dihydro-2H-1,4-benzothiazin-3-one | 121–123 |
| 19 | 5-(3-Chloropropoxy)-8-methyl-1,2-dihydroquinolin-2-one | 162–165 |
| 20 | 6-(3-Chloropropoxy)-1,2-dihydro-quinolin-2-one | 196–198 |
| 21 | 7-(2-Chloroethoxy)-1,2-dihydro-quinolin-2-one | 182–184 |
| 22 | 7-(3-Chloroethoxy)-1,2-dihydro-quinolin-2-one | 124–126 |
| 23 | 5-(2-Chloroethoxy)-8-methyl-1,2,3,4-tetrahydroquinolin-2-one | 161–162 |
| 24 | 5-(3-Chloropropoxy)-8-methyl-1,2,3,4-tetrahydroquinolin-2-one- | 146–147 |
| 25 | 5-(4-Chlorobutoxy)-8-methyl-1,2,3,4-tetrahydroquinolin-2-one | 120–121 |
| 26 | 5-(5-Chloropentyloxy)-8-methyl-1,2,3,4-tetrahydroquinolin-2-one | 115–116 |
| 27 | 6-(2-Chloroethoxy)-1,2,3,4-tetrahydroquinolin-2-one | 150–152 |
| 28 | 6-(3-Chloropropoxy)-1,2,3,4-tetrahydroquinolin-2-one | 133–135 |
| 29 | 6-(4-Chlorobutoxy)-1,2,3,4-tetrahydroquinolin-2-one | 146–147 |
| 30 | 6-(5-Chloropentyloxy)-1,2,3,4-tetrahydroquinolin-2-one | 102–104 |
| 31 | 7-(2-Chloroethoxy)-1,2,3,4-tetrahydroquinolin-2-one | 137–138 |
| 32 | 7-(3-Chloropropoxy)-1,2,3,4-tetrahydroquinolin-2-one | 126–127 |
| 33 | 7-(4-Chlorobutoxy)-1,2,3,4-tetrahydroquinolin-2-one | 104–105 |
| 34 | 7-(5-Chloropentyloxy)-1,2,3,4-tetrahydroquinolin-2-one | 130–131 |

TABLE 3

| Prep. Ex. | Compound Name | Melting point (° C.) |
|---|---|---|
| 35 | 7-(3-Chloropropoxy)-4,4-tetrahydro-quinolin-2-one | 147–148 |
| 36 | 8-(3-Chloropropoxy)-1,2,3,4-tetrahydroquinolin-2-one | 151–153 |
| 37 | 8-(4-Chloropropoxy)-1,2,3,4-tetrahydroquinolin-2-one | 129–131 |
| 38 | 4-(3-Chloropropoxy)-2,3-dihydro-1H-indol-2-one | 142–144 |
| 39 | 4-(2-Chloroethoxy)-3,3,7-trimethyl-2,3-dihydro-1H-indol-2-one | 153–154 |
| 40 | 4-(3-Chloropropoxy)-3,3,7-trimethyl-2,3-dihydro-1H-indol-2-one | 185–187 |
| 41 | 4-(4-Chlorobutoxy)-3,3,7-trimethyl-2,3-dihydro-1H-indol-2-one | 161–162 |
| 42 | 4-(5-Chloropentyloxy)-3,3,7-trimethyl-2,3-dihydro-1H-indol-2-one | 142–143 |
| 43 | 4-(3-Chloropropoxy)-3,3-dimethyl-2,3-dihydro-1H-indol-2-one | 149–151 |
| 44 | 5-(2-Chloroethoxy)-3,3-dimethyl-2,3-dihydro-1H-indol-2-one | 153–155 |
| 45 | 5-(3-Chloropropoxy)-3,3-dimethyl-2,3-dihydro-1H-indol-2-one | 102 |
| 46 | 5-(4-Chlorobutoxy)-3,3-dimethyl-2,3-dihydro-1H-indol-2-one | 94 |
| 47 | 5-(5-Chloropentyloxy)-3,3-dimethyl-2,3-dihydro-1H-indol-2-one | 94–95 |
| 48 | 6-(2-Chloroethoxy)-3,3-dimethyl-2,3-dihydro-1H-indol-2-one | 139–140 |
| 49 | 6-(3-Chloropropoxy)-3,3-dimethyl-2,3-dihydro-1H-indol-2-one | 130–131 |
| 50 | 6-(4-Chlorobutoxy)-3,3-dimethyl-2,3-dihydro-1H-indol-2-one | 126 |
| 51 | 6-(5-Chloropentyloxy)-3,3-dimethyl-2,3-dihydro-1H-indol-2-one | 156–157 |
| 52 | 7-(3-Chloropropoxy)-3,3-dimethyl-2,3-dihydro-1H-indol-2-one | 170–171 |
| 53 | 7-(4-Chlorobutoxy)-3,3-dimethyl-2,3-dihydro-1H-indol-2-one | 158–159 |

TABLE 3-continued

| Prep. Ex. | Compound Name | Melting point (° C.) |
|---|---|---|
| 54 | 7-(5-Chloropentyloxy)-3,3-dimethyl-2,3-dihydro-1H-indol-2-one | 110–111 |
| 55 | 7-(3-Chloropropoxy)-3,4-dihydro-2H-1,4-benzothiazin-3-one-1-oxide | 180–182 (dec.) |
| 56 | 7-(3-Chloropropoxy)-3,4-dihydro-2H-1,4-benzothiazin-3-one-1,1-dioxide | 172–174 |

Preparation Example 57

Synthesis of 1-(3-chloropropyl)-4-(2-quinolylmethyl) piperazine

A mixture consisting of 1-(2-quinolylmethyl)piperazine (21.75 g, 95.7 mmol), potassium carbonate (19.90 g, 144 mmol), 1-bromo-3-chloropropane (16.57 g, 105 mmol) and acetone (250 ml) was heated under reflux and stirring for 20 hours, insoluble matter was removed and the solvent was distilled off. The oil residue was dissolved in chloroform and the resulting solution was then subjected to chromatography on a silica gel column (developer: chloroform/methanol= 100/1), whereby 19.10 g of the title compound were obtained as a yellow oil (yield: 65.7%).

$^1$H-NMR(CDCl$_3$)δ(ppm): 8.12(1H,d,J=8.8 Hz), 8.08(1H, d,J=9.8 Hz), 7.80(1H,d,J=8.3 Hz), 7.70(1H,td,J=5.9,1.5 Hz), 7.63(1H,d,J=8.3 Hz), 7.51(1H,t,J=6.8 Hz), 3.85(2H,s), 3.59 (2H,t,J=6.3 Hz), 2.72–2.40(10H,m), 2.10–1.80(2H,m).

IR(film)cm$^{-1}$: 2940, 2812, 1600, 1504, 1458, 1425, 1299, 1160, 1132, 1013, 838, 757.

Preparation Example 58

Synthesis of 1-(3-chloropropyl)-4-(2-quinolylmethyl) homopiperazine

In a similar manner as in Preparation Example 57, the title compound was obtained as a pale amber oil from 1-(2-quinolymethyl)homopiperazine (yield: 76.1%).

$^1$H-NMR(CDCl$_3$)δ(ppm): 8.12(1H,d,J=8.3 Hz), 8.06(1H, d,J=8.8 Hz), 7.80(1H,d,J=7.8 Hz), 7.75–7.59(1H,m), 7.70 (1H,t,J=8.3 Hz), 7.50(1H,td,J=8.3,1.0 Hz), 3.97(2H,s), 3.61 (2H,t,J=6.3 Hz), 2.85–2.55(10 H,m), 2.00–1.72(4H,m).

IR(film)cm$^{-1}$: 2938, 2815, 1600, 1504, 1425, 1356, 1115, 832.

Preparation Example 59

Synthesis of 1-(1-chloroacetyl)-4-(2-quinolylmethyl) piperazine

After a mixture consisting of 1-(2-quinolylmethyl) piperazine (12.40 g, 54.6 mmol), chloroacetyl chloride (6.17 g, 54.6 mmol), triethylamine (5.52 g, 54.6 mmol) and acetone (200 ml) was stirred at room temperature for 1 hour, insoluble matter was removed and the solvent was then distilled off. The oil residue was dissolved in chloroform and the resulting solution was then subjected to chromatography on a silica gel column (developer: chloroform), whereby 12.62 g of the title compound were obtained as an amber oil (yield: 76.1%).

$^1$H-NMR(CDCl$_3$)δ(ppm): 8.15(1H,d,J=8.5 Hz), 8.08(1H, d,J=8.3 Hz), 7.81(1H,d,J=8.3 Hz), 7.70(1H,td,J=6.8 Hz,1.5 Hz), 7.61(1H,d,J=8.6 Hz), 7.53(1H,t,J=8.0 Hz), 4.06(2H,s), 3.88(2H,s), 3.68(2H,t,J=5.1 Hz), 3.56(2H,t,J=5.1 Hz), 2.60 (4H,qw,J=4.8 Hz).

IR(film)cm$^{-1}$: 2941, 2809, 1712, 1663, 1618, 1600, 1504, 1461, 1426, 1366, 1329, 1302, 1279, 1252, 1223, 1142, 1002, 835, 786, 757.

Preparation Example 60

Synthesis of 1-benzyl-4-(2-quinolylcarbonyl)piperazine hydrochloride

Thionyl chloride (6 ml) was added to a suspension of quinaldinic acid (3.463 g, 20 mmol) in chloroform (40 ml). After the resulting mixture was heated under reflux and stirring for 6 hours, the solvent was distilled off. The residue was dissolved in acetone (50 ml), followed by the addition of a solution of N-benzylpiperazine (10.576 g, 60 mmol) in acetone (50 ml). The thus-obtained mixture was stirred for 1 hour. A deposited precipitate was removed, and the solvent was distilled off. The residue was dissolved in ethyl ether. The resulting solution was washed with an aqueous solution of sodium chloride, and then dried over anhydrous magnesium sulfate. The solvent was distilled off, and the residue was dissolved in methanol, followed by the addition of concentrated hydrochloric acid (5 ml) for acidification. The solvent was distilled off and the thus-obtained residue was crystallized from a mixed solvent of ethanol and methanol, whereby 7.166 g of the title compound were obtained as white powder (yield: 97.5%).

m.p.: 235–237° C. (dec.)

$^1$H-NMR(DMSO-d$_6$)δ(ppm): 11.68(1H,br.s), 8.55(1H,d, J=8.3 Hz), 8.06(1H,d,J=9.8 Hz), 7.92–7.55(6H,m), 7.52–7.37(3H,m), 4.65(1H,d,J=12 Hz), 4.37(2H,s), 4.18 (1H,d,J=12 Hz), 3.85–3.00(6H,m).

IR(KBr)cm$^{-1}$: 2800–2200, 1644, 1474, 1416, 1290, 1100, 1040, 953, 838, 778, 770, 759, 704.

Preparation Example 61

Synthesis of 1-(2-quinolylcarbonyl)piperazine hydrochloride

After a mixture consisting of 1-benzyl-4-(2-quinolylcarbonyl)piperazine hydrochloride (18.81 g, 51.1 mmol), 10% palladium-charcoal catalyst (3.00 g) and water (150 ml) was stirred for 3 hours at a bath temperature of 70° C. under a hydrogen gas stream, the catalyst was removed and the solvent was then distilled off. The residue was crystallized from ethanol, whereby 11.03 g of the title compound were obtained as colorless prisms (yield: 77.7%).

m.p.: 236–237° C. (dec.)

$^1$H-NMR(DMSO-d$_6$)δ(ppm): 9.48(1H,br.s), 8.55(1H,d,J= 8.8 Hz), 8.07(2H,d,J=8.3 Hz), 7.91–7.64(3H,m), 4.02–3.70 (4H,br), 3.30–3.02(4H,br).

IR(KBr)cm$^{-1}$: 2938, 2744, 2716, 2711, 2475, 1647, 1593, 1472, 1436, 1421, 1289, 843, 789, 767.

Preparation Example 62

Synthesis of 1-(2-quinolylcarbonyl)piperazine 1-(2-Quinolylcarbonyl)piperazine hydrochloride (6.18 g, 22.2 mmol) was dissolved in water. The thus-obtained solution was rendered basic with a concentrated aqueous solution of sodium hydroxide. The resulting mixture was extracted with chloroform, and the extract was washed with an aqueous solution of sodium chloride and then dried over anhydrous magnesium sulfate. The solvent was distilled off, whereby 4.236 g of the title compound were obtained as a colorless oil (yield: 79.1%).

$^1$H-NMR(CDCl$_3$)δ(ppm): 8.27(1H,d,J=8.3 Hz), 8.11(1H, d,J=8.3 Hz), 7.91–7.57(4H,m), 3.87(2H,t,J=5.4 Hz), 3.66 (2H,t,J=5.4 Hz), 3.04(2H,t,J=5.4 Hz).

IR(KBr)cm$^{-1}$: 3301, 2947, 2917, 1629, 1597, 1561, 1479, 1441, 1424, 1288, 1173, 1140, 1118, 1024, 845, 819, 776, 764, 621.

Example 1

Synthesis of 3,3-dimethyl-5-{2-[4-(2-quinolylmethyl)-1-piperazinyl]ethoxy}-2,3-dihydro-1H-indol-2-one 5-(2-Chloroethoxy)-3,3-dimethyl-2,3-dihydroindol-2-one (182 mg, 3.0 mmol) and N—(2-quinolylmethyl)piperazine (690 mg, 3.0 mmol) were mixed, followed by stirring at 150° C. for 3 hours under an argon gas stream. The resulting mixture was allowed to cool down, and was then dissolved in chloroform. The thus-obtained solution was washed with water and then dried over anhydrous sodium sulfate. After the solution was concentrated under reduced pressure, the residue was purified by chromatography on a silica gel column while using chloroform-methanol (10:1) as an eluent. Fractions containing the target compound were collected and then concentrated under reduced pressure. The concentrate was crystallized from n-hexane and was then recrystallized from ethyl acetate-ethyl ether, whereby 240 mg of the title compound were obtained as pale yellow powder (yield: 73%).

m.p.: 187–189° C. (dec.)

$^1$H-NMR(CDCl$_3$)δ(ppm): 8.57(1H,br.s), 8.12(1H,d,J=8.5 Hz), 8.07(1H,d,J=8.8 Hz), 7.80(1H,d,J=8.3 Hz), 7.69(1H,dt, J=8.6,1.5 Hz), 7.63(1H,d,J=8.3 Hz), 7.51(1H,dt,J=8.1,1.2 Hz), 6.80(1H,d,J=8.4 Hz), 6.80(1H,d,J=2.4 Hz), 6.71(1H, dd,J=8.4,2.4 Hz), 4.08(2H,t,J=5.9 Hz), 3.86(2H,s), 2.82(2H, t,J=5.9 Hz), 2.65(8H,br.s), 1.37(6H,s).

IR(KBr)cm$^{-1}$: 3424, 3171, 3088, 3045, 2965, 2927, 2870, 2810, 1709, 1603, 1566, 1500, 1482, 1456, 1427, 1393, 1331, 1311, 1278, 1206, 1158, 1135, 1091, 1076, 1050, 1014, 973, 958, 870, 854, 840, 824, 761, 737, 653, 579, 482, 459.

Example 2

Synthesis of 3,3,7-trimethyl-4-{3-[4-(N-ethoxyethylbenzoimidazol-2-ylmethyl)-1-piperazinyl]-propoxy}-2,3-dihydro-1H-indol-2-one dimaleate A mixture consisting of 3,3,7-trimethyl-4-(3-chloropropoxy)-2,3-dihydro-1H-indol-2-one (268 mg, 1.00 mmol) and 1-(N-ethoxyethylbenzoimidazol-2-ylmethyl) piperazine (1.15 g, 4.00 mmol) was stirred for 4 hours at a bath temperature of 150° C. under an argon gas stream. The reaction mixture was dissolved in chloroform. The thus-obtained solution was washed with water, dried over anhydrous sodium sulfate, and then concentrated under reduced pressure. The residue was purified by subjecting it to chromatography on a silica gel column (developer: chloroform/methanol(saturated with ammonia)=20/1). Fractions containing the target compound were collected and then concentrated under reduced pressure, whereby 458 mg of the free base of the title compound were obtained as an amber oil (88.1%). The oil was dissolved in methanol, to which anhydrous maleic acid (205 mg, 1.77 mmol) was added to convert the free base into its dimaleate. The dimaleate was then recrystallized from a mixed solvent of methanol and acetone, whereby 512 mg of the title compound were obtained as white powder (yield: 77.3%).

m.p.: 163–165° C. (dec.)

$^1$H-NMR(CDCl$_3$)δ(ppm): 10.30(1H,s), 7.61(1H,m), 7.58 (1H,m), 7.27(1H,m), 7.21(1H,m), 6.91(1H,d,J=8.5 Hz), 6.50 (1H,d,J=8.5 Hz), 6.14(4H,s), 4.52(1H,br.t,J=5.1 Hz), 4.08–3.96(4H,m), 3.72(2H,br.t,J=5.1 Hz), 3.39(2H,q,J=7.1 Hz), 3.50–2.80(8H,br), 3.22(2H,br), 2.14(3H,s), 1.31(6H,s), 1.04(3H,t,J=7.1 Hz).

IR(KBr)cm$^{-1}$: 2977, 2869, 1705, 1614, 1582, 1509, 1485, 1465, 1385, 1361, 1091, 866.

Example 3

Synthesis of 7-{3-[4-(2-quinolylmethyl)-1-piperazinyl]propoxy}-2,3,4,5-tetrahydro-1H-1-benzoazepin-2-one A mixture consisting of 7-(3-chloropropoxy)-2,3,4,5-tetrahydro-1H-benzoazepin-2-one (0.304 g, 1.2 mmol) and 1-(2-quinolylmethyl)piperazine (1.091 g, 4.8 mmol) was stirred for 4 hours at a bath temperature of 150° C. under an argon gas stream. The reaction mixture was dissolved in chloroform. The thus-obtained solution was rendered basic with a dilute aqueous solution of sodium hydroxide, washed with water, and then dried over magnesium sulfate. After the resulting solution was purified by subjecting it to chromatography on a silica gel column (developer: chloroform/methanol=40/1), recrystallization was conducted from acetone. The title compound (0.270 g) was obtained as yellow prisms (yield: 50.6%).

m.p.: 131–133° C.

$^1$H-NMR(CDCl$_3$)δ(ppm): 8.10(2H,t,J=8.8 Hz), 7.85–7.44 (1H,m),7.32(1H,br.s), 6.92–6.66(3H,m), 4.00(2H,t,J=6.3 Hz), 3.86(2H,s), 2.75(2H,t,J=7.3 Hz), 2.68–2.40(10H,m), 2.40–2.07(4H,m), 2.05–1.88(2H,m).

IR(KBr)cm$^{-1}$: 1672, 1499, 1424, 1385, 1255, 1238, 1170, 1163, 1155, 1057, 835, 807, 749.

Example 4

Synthesis of 7-{3-[4-(2-quinolylmethyl)-1-piperazinyl]propoxy}-2,3,4,5-tetrahydro-1H-2-benzoazepin-1-one A mixture consisting of 7-(chloropropoxy)-2,3,4,5-tetrahydro-1H-2-benzoazepin-1-one (0.507 g, 2 mmol) and 1-(2-quinolylmethyl)piperazine (1.81 g, 8 mmol) was stirred for 4 hours at a bath temperature of 150° C. under an argon gas stream. After the reaction mixture was allowed to cool down, chloroform was added to the reaction mixture to dissolve the same. The resulting solution was rendered basic with a dilute aqueous solution of sodium hydroxide. The thus-obtained solution was washed with water and then dried over anhydrous magnesium sulfate. After the resulting solution was purified by subjecting it to chromatography on a silica gel column (developer: chloroform/methanol=40/1), recrystallization was conducted from acetone. The title compound (0.613 g) was obtained as yellow leaflets (yield: 68.9%).

m.p.: 161–162° C.

$^1$H-NMR(CDCl$_3$)δ(ppm): 8.11(2H,t,J=8.8 Hz), 7.78(1H, td,J=9.8,1.5 Hz), 7.75–7.58(4H,m), 7.51(1H,td,J=6.9,1.0 Hz), 6.84(1H,dd,J=8.3,2.4 Hz), 6.71(1H,d,J=2.4 Hz), 6.52–6.34(1H,br), 4.05(2H,t,J=6.4 Hz), 3.86(2H,s), 3.12 (2H,t,J=6.4 Hz), 2.83(2H,t,J=6.8 Hz), 2.72–2.40(10H,m), 2.09–1.88(4H,m).

IR(KBr)cm$^{-1}$: 2940, 2805, 1652, 1601, 1246.

Example 5

Synthesis of 7-{3-[4-(2-quinolylmethyl)-1-piperazinyl]propoxy}-3,4-dihydro-2H-1,4-benzothiazin-3-one-1-oxide A mixture consisting of 7-(3-chloropropoxy)-3,4-dihydro-2H-1,4-benzothiazin-3-one-1-oxide (2.02 g, 7.38 mmol), N-(2-quinolylmethyl)piperazine (2.52 g, 11.07 mmol), potassium carbonate (2.04 g, 14.76 mmol), potassium iodide (2.45 g, 14.76 mmol) and DMF (50 ml) was stirred at 80° C. for 4 hours. The solvent was distilled off from the reaction mixture under reduced pressure, followed by the addition of water. The resulting mixture was extracted with chloroform-methanol (10:1). The extract was dried over anhydrous sodium sulfate and then concentrated under reduced pressure. The residue was purified by chromatography on a silica gel column while using chloroform-ammonia-saturated methanol (10:1) as an eluent. Fractions containing the target compound were collected and then concentrated under reduced pressure, whereby 1.23 g of the title compound was obtained as a yellow oil (4.49 mmol, 60.9%).

$^1$H-NMR(CDCl$_3$)δ(ppm): 8.89(1H,br.s), 8.13(1H,d,J=8.6 Hz), 8.07(1H,d,J=8.6 Hz), 7.81(1H,d,J=8.1 Hz), 7.70(1H, ddd,J=8.6,7.1,1.5 Hz), 7.63(1H,d,J=8.6 Hz), 7.52(1H,ddd, J=8.1,6.8,1.2 Hz), 7.25(1H,d,J=2.7 Hz), 7.06(1H,dd,J=8.8, 2.7 Hz), 6.97(1H,d,J=8.8 Hz), 4.12(1H,d,J=5.4 Hz), 4.04 (2H,t,J=6.4 Hz), 3.87(2H,s), 3.66(1H,d,J=5.4 Hz), 2.70–2.42(10H,cm), 2.00(2H,br).

IR(KBr)cm$^{-1}$: 2940, 2816, 1686, 1500, 1228, 1039.

Examples 6–49

In a similar manner as in Examples 1–5, the compounds shown in Tables 4–6 were obtained. Some of the compounds were converted into salts with maleic acid by a method known per se in the art.

TABLE 4

| Ex. | Compound Name | Melting point (° C.) |
|---|---|---|
| 6 | 7-{3-[4-(2-Quinazolinylmethyl)-1-piperazinyl]propoxy}-3,4-dihydro-2H-1,4-benzothiazin-3-one | 155–157 |
| 7 | 3,3,7-Trimethyl-4-{4-[4-(2-quinolyl-methyl)-1-piperazinyl]butoxy}-2,3-dihydro-1H-indol-2-one | 148–149 |
| 8 | 7-{5-[4-(2-Quinolylmethyl)-1-piperazinyl]pentyloxy}-3,4-dihydro--2H-1,4-benzothiazin-3-one | 150–151 |
| 9 | 3,3,7-Trimethyl-4-{5-[4-(2-quinolyl-methyl)-1-piperazinyl]pentyloxy}-2,3-dihydro-1H-indol-2-one | 141–146 |
| 10 | 7-{4-[4-(2-Quinolylmethyl)-1-piperazinyl]butoxy}-3,4-dihydro-2H-1,4-benzothiazin-3-one | 152–153 |
| 11 | 4-{3-[4-(2-Quinolylmethyl)-1-piperazinyl]propoxy}-2,3-dihydro-1H-indol-2-one | 159–160 |
| 12 | 8-Methyl-5-{2-[4-(2-quinolylimethyl)-1-piperazinyl]ethoxy}-1,2,3,4-tetrahydroquinolin-2-one | 149–150 |
| 13 | 8-Methyl-5-{4-[4-(2-quinolylmethyl)-1-piperazinyl]butoxy}-1,2,3,4-tetrahydroquinolin-2-one | 115–117 |
| 14 | 8-Methyl-5-{5-[4-(2-quinolylmethyl)-1-piperazinyl]pentyloxy}-1,2,3,4-tetrahydroquinolin-2-one | 147–148 |
| 15 | 6-{3-[4-(2-Quinolylmethyl)-1-piperazinyl]propoxy}-2,3,4,5-tetrahydro-1H-1-benzoazepin-2-one | 130–131 |
| 16 | 3,3-Dimethyl-5-{3-[4-(2-quinolyl-methyl)-1-piperazinyl]propoxy}-2,3-dihydro-1H-indol-2-one | 137–138 |
| 17 | 3,3-Dimethyl-5-{4-[4-(2-quinolyl-methyl)-1-piperazinyl]butoxy}-2,3-dihydro-1H-indol-2-one | 119–120 |
| 18 | 3,3-Dimethyl-5-{5-[4-(2-quinolyl-methyl)-1-piperazinyl]pentyloxy}-2,3-dihydro-1H-indol-2-one | 109–110 |
| 19 | 6-{2-[4-(2-Quinolylmethyl)-1-piperazinyl]ethoxy}-1,2,3,4-tetrahydroquinolin-2-one | 154–156 |
| 20 | 6-{3-[4-(2-Quinolylmethyl)-1-piperazinyl]propoxy}-1,2,3,4-tetrahydroquinolin-2-one | 176–178 |
| 21 | 6-{4-[4-(2-Quinolylmethyl)-1-piperazinyl]butoxy}-1,2,3,4-tetrahydroquinolin-2-one | 150–152 |

TABLE 5

| Ex. | Compound Name | Melting point (° C.) |
|---|---|---|
| 22 | 6-{5-[4-(2-Quinolylmethyl)-1-piperazinyl]pentyloxy}-1,2,3,4-tetrahydroquinolin-2-one | 140–142 |
| 23 | 4,4-Dimethyl-7-{3-[4-(2-quinolyl-methyl)-1-piperazinyl]propoxy}-1,2,3,4-tetrahydroquinolin-2-one | 190–192 (dec.)[a] |
| 24 | 3,3,7-Trimethyl-4-{3-[4-(2-quinazolinylmethyl)-1-piperazinyl]-propoxy}-2,3-dihydro-1H-indol-2-one | 162–164 |
| 25 | 8-Methyl-5-{3-[4-(2-quinazolinyl-methyl)-1-piperazinyl]propoxy)-1,2,3,4-tetrahydroquinolin-2-one | 145–147 |
| 26 | 3,3,7-Trimethyl-4-{3-[4-(N-methyl-benzoimidazol-2-ylmethyl)-1-piperazinyl]propoxy}-2,3-dihydro-1H-indol-2-one | 150–153 (dec.)[a] |
| 27 | 7-{3-[4-(N-Methylbenzoimidazol-2-ylmethyl)-1-piperazinyl]propoxy}-3,4-dihydro-2H-1,4-benzothiazin-3-one | 176–179 (dec.)[a] |
| 28 | 7-{3-[4-(N-Ethoxyethylbenzoimidazol-2-ylmethyl)-1-piperazinyl]propoxy}-3,4-dihydro-2H-1,4-benzothiazin-3-one | 178–181 (dec.)[a] |
| 29 | 3,3-Dimethyl-7-{3-[4-(2-quinolyl-methyl)-1-piperazinyl]propoxy}-2,3-dihydro-1H-indol-2-one | 111–112 |
| 30 | 3,3-Dimethyl-7-{4-[4-(2-quinolyl-methyl)-1-piperazinyl]butoxy}-2,3-dihydro-1H-indol-2-one | 133–134 |
| 31 | 6-{3-[4-(2-Quinolylmethyl)-1-piperazinyl]propoxy}-1,2-dihydro-quinolin-2-one | 169–171 |
| 32 | 7-{2-[4-(2-Quinolylmethyl)-1-piperazinyl]ethoxy}-1,2,3,4-tetrahydroquinolin-2-one | 148–150 |
| 33 | 7-{3-[4-(2-Quinolylmethyl)-1-piperazinyl]propoxy}-1,2,3,4-tetrahydroquinolin-2-one | 199–200 (dec.)[a] |
| 34 | 7-{4-[4-(2-Quinolylmethyl)-1-piperazinyl]butoxy}-1,2,3,4-tetrahydroquinolin-2-one | 145–147 |
| 35 | 7-{5-[4-(2-Quinolylmethyl)-1-piperazinyl]pentyloxy}-1,2,3,4-tetrahydroquinolin-2-one | 116–117 |
| 36 | 7-{3-[4-(2-Quinolylmethyl)-1-piperazinyl]propoxy}-1,2-dihydroquinolin-2-one | 155–157 |

*[a]dimaleate

TABLE 6

| Ex. | Compound Name | Melting point (° C.) |
|---|---|---|
| 37 | 3,3,7-Trimethyl-4-{5-[4-(2-quinolyl-methyl)-1-piperazinyl]pentyloxxy}-2,3-dihydro-1H-indol-2-one | 121–122 |
| 38 | 3,3-Dimethyl-6-{3-[4-(2-quinolyl-methyl)-1-piperazinyl]propoxy}-2,3-dihydro-1H-indol-2-one | 143–144 |
| 39 | 7-{2-[4-(2-Quinolylmethyl)-1-piperazinyl]ethoxy}-1,2-dihydro-quinolin-2-one | 188–190 (dec.) |
| 40 | 3,3-Dimethyl-6-{2-[4-(2-quinolyl-methyl)-1-piperazinyl]ethoxy}-2,3-dihydro-1H-indol-2-one | 161–162 |
| 41 | 3,3-Dimethyl-4-{3-[4-(2-quinolyl-methyl)-1-piperazinyl]propoxy}-2,3-dihydro-1H-indol-2-one | 162–163 |
| 42 | 3,3-Dimethyl-6-{5-[4-(2-quinolyl-methyl)-1-piperazinyl]pentyloxy}-2,3-dihydro-1H-indol-2-one | 144–145 |

TABLE 6-continued

| Ex. | Compound Name | Melting point (° C.) |
|---|---|---|
| 43 | 3,3-Dimethyl-6-{4-[4-(2-quinolyl-methyl)-1-piperazinyl]butoxy}-2,3-dihydro-1H-indol-2-one | 138–140 |
| 44 | 8-{4-[4-(2-Quinolylmethyl)-1-piperazinyl]butoxy}-1,2,3,4-tetrahydroquinolin-2-one | 174–177 (dec.)[a] |
| 45 | 8-{3-[4-(2-Quinolylmethyl)-1-piperazinyl]propoxy}-1,2,3,4-tetrahydroquinolin-2-one | 172 (dec.)[a] |
| 46 | 7-{3-[4-(2-Quinolylmethyl)-1-piperazinyl]propoxy}-3,4-dihydro-2H-1,4-benzothiazin-3-one-1,1-dioxide | 204–206 (dec.) |
| 47 | 7-{3-[4-(4-Benzyloxy-2-quinolyl-methyl)-1-piperazinyl]propoxy}-3,4-dihydro-2H-1,4-benzothiazin-3-one | 151–154 |
| 48 | 7-{3- [4-(8-Benzyloxy-2-quinolyl-methyl)-1-piperazinyl]propoxy}-3,4-dihydro-2H-1,4-benzothiazin-3-one-1,1-dioxide | Amorphous |
| 49 | 7-{3-[4-(1-Oxo-2-quinolylmethyl)-1-piperazinyl]propoxy}-3,4-dihydro-2H-1,4-benzothiazin-3-one-1,1-dioxide | 175–177 (dec.) |

*[a]dimaleate

Example 50

Preparation of 3,3-dimethyl-5-{2-[4-(2-quinolylmethyl)-1-homopiperazinyl]ethoxy}-2,3-dihydro-1H-indol-2-one dimaleate 5-(2-Chloroethoxy)-3,3-dimethyl-2,3-dihydroindol-2-one (214 mg, 0.89 mmol) and N-(2-quinolylmethyl)homopiperazine (1.07 mg, 4.45 mmol) were mixed, followed by stirring at 150° C. for 3 hours under an argon gas stream. The reaction mixture was allowed to cool down, and was then dissolved in chloroform. The resulting solution was washed with water and then dried over anhydrous sodium sulfate. After the solution was concentrated under reduced pressure, the residue was purified by chromatography on a silica gel while using chloroform-methanol (10:1) as an eluent. Fractions containing the target compound were collected and then concentrated under reduced pressure, whereby 127 mg of the free base of the title compound were obtained as an amber oil (32%). The oil was dissolved in methanol, to which anhydrous maleic acid (66 mg, 0.57 mmol) was added to convert the free base into its dimaleate. The dimaleate was crystallized from ethyl ether, whereby 170 mg of the title compound were obtained as pale yellow powder (yield: 28%).

m.p.: 145–147° C. (dec.)

$^1$H-NMR(DMSO-$d_6$)δ(ppm): 8.40(1H,d,J=8.6 Hz), 8.01–7.98(2H,m), 7.78(1H,dt,J=8.3,1.5 Hz), 7.68–7.59(2H, m), 6.99(1H,br.s), 6.78–6.77(2H,m), 6.13(4H,s), 4.25(2H,s), 4.21(2H,t,J=5.1 Hz), 3.45–3.16(8H,br.s), 3.03(2H,t,J=5.1 Hz), 2.06–2.00(2H,m), 1.23(6H,s).

IR(KBr)cm$^{-1}$: 1717, 1695, 1674, 1577, 1483, 1386, 1363, 1280, 1202, 1088, 1006, 930, 877, 865, 833, 814, 710, 571.

Example 51

Synthesis of 7-{3-[4-(N-methylbenzoimidazol-2-ylmethyl)-1-homopiperazinyl]propoxy}-3,4-dihydro-2H-1,4-benzothiazin-3-one A mixture consisting of 7-(3-chloropropoxy)-3,4-dihydro-2H-1,4-benzothiazin-3-one (303 mg, 1.18 mmol) and 1-(N-methylbenzoimidazol-2-ylmethyl-1-homopiperazine (4.71 mmol) was stirred for 4 hours at a bath temperature of 120° C. under an argon gas stream. The reaction mixture was dissolved in chloroform. The resulting solution was washed with water, dried over anhydrous sodium sulfate, and then concentrated under reduced pressure. The residue was subjected to chromatography on a silica gel column (developer: chloroform/methanol (saturated with ammonia)=20/1) for purification. Recrystallization was then conducted from a mixed solvent of chloroform and ethyl ether, whereby 507 mg of the title compound were obtained as colorless needles (yield: 92.3%).

m.p.: 123–125° C.

$^1$H-NMR(CDCl$_3$)δ(ppm): 9.04(1H,s), 7.72(1H,m), 7.37–7.20(3H,m), 6.84(1H,d,J=2.7 Hz), 6.80(1H,d,J=8.8 Hz), 6.70(1H,dt,J=8.8,2.7 Hz), 3.95(2H,t,J=6.4 Hz), 3.92 (2H,s), 3.89(3H,s), 3.40(2H,s), 2.80–2.58(10H,m), 1.95–1.74(4H,m).

IR(KBr)cm$^{-1}$: 2940, 1668, 1607, 1498, 1475, 1237, 1120, 1069, 832, 737.

Examples 52–89

In a similar manner as in Examples 50 and 51, the compounds shown in Tables 7–9 were obtained. Some of the compounds were converted into salts with maleic acid or oxalic acid by a method known per se in the art.

TABLE 7

| Ex. | Compound Name | Melting point (° C.) |
|---|---|---|
| 52 | 7-{5-[4-(2-Quinolylmethyl)-1-homopiperazinyl]pentyloxy}-3,4-dihydro-2H-1,4-benzothiazin-3-one | 97–99 |
| 53 | 3,3,7-Trimethyl-4-{5-[4-(2-quinolylmethyl)-1-homopiperazinyl]pentyloxy}-2,3-dihydro-1H-indol-2-one | 90–91 |
| 54 | 3,3,7-Trimethyl-4-{2-[4-(2-quinolylmethyl)-1-homopiperazinyl]ethoxy}-2,3-dihydro-1H-indol-2-one | 153–155 (dec.)[a] |
| 55 | 3,3,7-Trimethyl-4-{4-[4-(2-quinolylmethyl)-1-homopiperazinyl]butoxy}-2,3-dihydro-1H-indol-2-one | 122–124 (dec.)[a] |
| 56 | 7-{2-[4-(2-Quinolylmethyl)-1-homopiperazinyl]ethoxy}-3,4-dihydro-2H-1,4-benzothiazin-3-one | 126–128 |
| 57 | 7-{4-[4-(2-Quinolylmethyl)-1-homopiperazinyl]ethoxy}-3,4-dihydro-2H-1,4-benzothiazin-3-one | 86–88 |
| 58 | 8-Methyl-5-{5-[4-(2-quinolylmethyl)-1-homopiperazinyl]pentyloxy}-1,2,3,4-tetrahydroquinolin-2-one | 143–145 (dec.)[a] |
| 59 | 8-Methyl-5-{4-[4-(2-quinolylmethyl)-1-homopiperazinyl]butoxy}-1,2,3,4-tetrahydroquinolin-2-one | 146–148 (dec.)[a] |
| 60 | 8-Methyl-5-{3-[4-(2-quinolylmethyl)-1-homopiperazinyl]propoxy}-1,2,3,4-tetrahydroquinolin-2-one | 154–156[a] |
| 61 | 8-Methyl-5-{2-[4-(2-quinolylmethyl)-1-homopiperazinyl]ethoxy}-1,2,3,4-tetrahydroquinolin-2-one | 156–157 (dec.)[a] |
| 62 | 3,3-Dimethyl-5-{3-[4-(2-quinolyl-methyl)-1-homopiperazinyl]propoxy}-2,3-dihydro-1H-indol-2-one | 139–140[a] |
| 63 | 6-{2-[4-(2-Quinolylmethyl)-1-homopiperazinyl]ethoxy}-1,2,3,4-tetrahydroquinolin-2-one | 139–141 (dec.)[a] |
| 64 | 6-{3-[4-(2-Quinolylmethyl)-1-homopiperazinyl]propoxy}-1,2,3,4-tetrahydroquinolin-2-one | 158–161 (dec.)[a] |
| 65 | 6-{4-[4-(2-Quinolylmethyl)-1-homopiperazinyl]butoxy}-1,2,3,4-tetrahydroquinolin-2-one | 159–161 (dec.)[a] |
| 66 | 6-{5-[4-(2-Quinolylmethyl)-1-homopiperazinyl]pentyloxy}-1,2,3,4-tetrahydroquinolin-2-one | 143–145 (dec.)[a] |

*[a]dimaleate

TABLE 8

| Ex. | Compound Name | Melting point (° C.) |
|---|---|---|
| 67 | 6-{3-[4-(2-Quinolylmethyl)-1-homo-piperazinyl]propoxy}-2,3,4,5-tetrahydro-1H-1-benzoazepin-2-one | 129–131 (dec.)[a] |
| 68 | 4,4-Dimethyl-7-{3-[4-(2-quinolyl-methyl)-1-homopiperazinyl]propoxy}-1,2,3,4-tetrahydroquinolin-2-one | 157–159 (dec.)[a] |
| 69 | 3,3-Dimethyl-7-{3-[4-(2-quinolyl-methyl)-1-homopiperazinyl]propoxy}-2,3-dihydro-1H-indol-2-one | 133–134 (dec.)[a] |
| 70 | 6-{3-[4-(2-Quinolylmethyl)-1-homo-piperazinyl]propoxy}-1,2-dihydro-quinolin-2-one | 161–163 (dec.)[a] |
| 71 | 7-{3-[4-(2-Quinolylmethyl)-1-homo-piperazinyl]propoxy}-1,2,3,4-tetrahydroquinolin-2-one | 158–160 (dec.)[a] |
| 72 | 7-{4-[4-(2-Quinolylmethyl)-1-homo-piperazinyl]butoxy}-1,2,3,4-tetrahydroquinolin-2-one | 153–155 (dec.)[a] |
| 73 | 7-{5-[4-(2-Quinolylmethyl)-1-homo-piperazinyl]pentyloxy}-1,2,3,4-tetrahydroquinolin-2-one | 143–145 (dec.)[a] |
| 74 | 7-{3-[4-(2-Quinolylmethyl)-1-homo-piperazinyl]propoxy}-1,2-dihydro-quinolin-2-one | 151–153 (dec.)[a] |
| 75 | 6-{2-[4-(N-Methylbenzoimidazol-2-ylmethyl)-1-homopiperazinyl]ethoxy}-1,2,3,4-tetrahydroquinolin-2-one | 146–147 (dec.)[a] |
| 76 | 8-Methyl-5-{2-[4-(N-methylbenzo-imidazol-2-ylmethyl)-1-homo-piperazinyl]ethoxy}-1,2,3,4-tetrahydroquinolin-2-one | 163–165 (dec.)[a] |
| 77 | 6-{2-[4-(N-Methylbenzoimidazol-2-ylmethyl)-1-homopiperazinyl]ethoxy}-1,2-dihydroquinolin-2-one | 166–169[a] |
| 78 | 3,3-Dimethyl-6-{3-[4-(2-quinolyl-methyl)-1-homopiperazinyl]propoxy}-2,3-dihydro-1H-indol-2-one | 132–135 (dec.)[a] |
| 79 | 7-{2-[4-(2-Quinolylmethyl)-1-homo-piperazinyl]ethoxy}-1,2-dihydro-quinolin-2-one | 151–153 (dec.)[a] |
| 80 | 7-{2-[4-(N-Methylbenzoimidazol-2-ylmethyl)-1-homopiperazinyl]ethoxy)-1,2-dihydroquinolin-2-one | 119–121 (dec.)[b] |
| 81 | 7-{2-[4-(2-Quinolylmethyl)-1-homo-piperazinyl]ethoxy}-1,2,3,4-tetrahydroquinolin-2-one | 155–157 (dec.)[a] |

*[a]dimaleate, *[b]dioxalate

TABLE 9

| Ex. | Compound Name | Melting point (° C.) |
|---|---|---|
| 82 | 7-{2-[4-(N-Methylbenzoimidazol-2-ylmethyl)-1-homopiperazinyl]ethoxy}-1,2,3,4-tetrahydroquinolin-2-one | 146–148 (dec.)[b] |
| 83 | 7-{3-[4-(N-Ethoxyethylbenzoimidazol-2-ylmethyl)-1-homopiperazinyl]-propoxy}-3,4-dihydro-2H-1,4-benzothiazin-3-one | 145–147[b] |
| 84 | 3,3-Dimethyl-6-{2-[4-(2-quinolyl-methyl)-1-homopiperazinyl]ethoxy}-2,3-dihydro-1H-indol-2-one | 170 (dec.)[a] |
| 85 | 3,3-Dimethyl-4-{3-[4-(2-quinolyl-methyl)-1-homopiperazinyl]propoxy}-2,3-dihydro-1H-indol-2-one | 201–204[b] |
| 86 | 7-{3-[4-(2-Quinolylmethyl)-1-homo-piperazinyl]propoxy}-2,3,4,5-tetrahydro-1H-1-benzoazepin-2-one | 130–132[a] |
| 87 | 7-{3-[4-(2-Quinolylmethyl)-1-homo-piperazinyl]propoxy}-2,3,4,5-tetrahydro-1H-2-benzoazepin-1-one | 150–152 (dec.)[a] |
| 88 | 8-{3-[4-(2-Quinolylmethyl)-1-homo-piperazinyl]propoxy}-1,2,3,4-tetrahydroquinolin-2-one | 159–161 (dec.)[a] |
| 89 | 8-{4-[4-(2-Quinolylmethyl)-1-homo-piperazinyl]butoxy}-1,2,3,4-tetrahydroquinolin-2-one | 148–150 (dec.)[a] |

*[a]dimaleate, *[b]dioxalate

Example 90

Synthesis of 7-{3-[4-(2-quinolylmethyl)piperazinyl]propoxy}-3,4-dihydro-2H- 1,4-benzothiazin-3-one After a mixture consisting of 7-hydroxy-3,4-dihydro-2H-1,4-benzothiazin-3-one (1.812 g, 10 mmol), tetra-n-butylammonium bromide (0.322 g, 1 mmol), potassium carbonate (2.764 g, 20 mmol), 1-(3-chloropropyl)-4-(2-quinolylmethyl)piperazine (3.039 g, 10 mmol) and N,N-dimethylformamide (40 ml) was stirred for 4 days at a bath temperature of 50° C. under an argon gas stream, the solvent was distilled off under reduced pressure. Water was added to the residue, followed by extraction with chloroform. The extract was washed with water and then dried over anhydrous magnesium sulfate. The extract was subjected to chromatography on a silica gel column (developer: chloroform/methanol=100/1 to 40/1) and then crystallized from ethyl acetate, whereby 1.188 g of the title compound were obtained as yellow prisms (yield: 26.5%).

m.p.: 159–161° C.

$^1$H-NMR(CDCl$_3$)δ(ppm): 8.52(1H,s), 8.10(2H,t,J=8.8 Hz), 7.80(1H,d,J=8.3 Hz), 7.70(1H,td,J=7.8,1.5 Hz), 7.63 (1H,d,J=8.3 Hz), 7.51(1H,t,J=6.8 Hz), 6.86(1H,d,J=2.4 Hz), 6.78(1H,d,J=8.8 Hz), 6.71(1H,dd,J=8.8,2.4 Hz), 3.97(2H,t, J=6.3 Hz), 3.86(2H,s), 3.41(2H,s), 2.72–2.34(10H,m), 1.91 (2H,q,J=6.8 Hz).

IR(KBr)cm$^{-1}$: 2944, 1816, 1683, 1493, 1211, 1070.

Example 91

Synthesis of 8-methyl-5-{3-[4-(2-quinolylmethyl)piperazinyl]propoxy}-1,2,3,4-tetrahydroquinolin-2-one After a mixture consisting of 5-hydroxy-8-methyl-1,2,3,4-tetrahydroquinolin-2-one (1.80 g, 10.2 mmol), tetra-n-butylammonium bromide (0.322 g, 1 mmol), potassium carbonate (4.146 g, 30 mmol), 1-(3-chloropropyl)-4-(2-quinolylmethyl)piperazine (3.67 g, 12.1 mmol) and N,N-dimethylformamide (40 ml) was stirred for 2 days at a bath temperature of 50° C. under an argon gas stream, the solvent was distilled off under reduced pressure. Water was added to the residue, followed by extraction with chloroform. The extract was washed with water and then dried over anhydrous magnesium sulfate. The extract was subjected to chromatography on a silica gel column (developer: chloroform/methanol=40/1) and then crystallized from ethyl acetate-n-hexane, whereby 0.773 g of the title compound was obtained as yellow leaflets (yield: 17.2%).

m.p.: 150–152° C. (dec.)

$^1$H-NMR(CDCl$_3$)δ(ppm): 8.13(1H,d,J=8.8 Hz), 8.10(2H, d,J=8.8 Hz), 7.85–7.44(4H,m), 7.37(1H,br.s), 6.95(1H,d,J=

8.3 Hz), 6.50(1H,d,J=8.3 Hz), 4.00(2H,t,J=6.3 Hz), 3.86 (2H,s), 2.95(2H,t,J=7.8 Hz), 2.70–2.40(12H,m), 2.16(3H,s), 2.06–1.82(2H,m).

IR(KBr)cm$^{-1}$: 3222, 2939, 2816, 1679, 1615, 1598, 1504, 1466, 1376, 1328, 1274, 1207, 1093, 838, 792, 752.

Examples 92–97

In a similar manner as in Examples 90 and 91, the compounds shown in Table 10 were obtained. The compound of Example 92 was converted into its dihydrochloride salt by a method known per se in the art.

TABLE 10

| Ex. | Compound Name | Melting point (° C.) |
|---|---|---|
| 92 | 3,3,7-(Trimethyl-4-{3-[4-(2-quinolyl-methyl)-1-piperazinyl]propoxy}-2,3-dihydro-1H-indol-2-one | 232–234 (dec.)*$^{c)}$ |
| 93 | 3,3,7-Trimethyl-4-{2-[4-(2-quinolyl-methyl)-1-piperazinyl]ethoxy}-2,3-dihydro-1H-indol-2-one | 133–135 |
| 94 | 7-{2-[4-(2-Quinolylmethyl)-1-piperazinyl]ethoxy}-3,4-dihydro-2H-1,4-benzothiazin-3-one | 171–173 (dec.) |
| 95 | 8-Methyl-5-{3-[4-(2-quinolylmethyl)-1-piperazinyl]propoxy}-1,2-dihydroquinolin-2-one | 170–172 |
| 96 | 7-{3-[4-(2-Quinolylmethyl)-1-homo-piperazinyl]propoxy}-3,4-dihydro-2H-1,4-benzothiazin-3-one | 130–132 |
| 97 | 3,3,7-Trimethyl-4-{3-[4-(2-quinolyl-methyl)-1-homopiperazinyl]propoxy}-2,3-dihydro-1H-indol-2-one | 110–112 |

*$^{c)}$dihydrochloride

Example 98

Synthesis of 7-(1-[4-(2-quinolylmethyl) piperazinylcarbonyl]methoxy}-3,4-dihydro-2H-1,4-benzothiazin-3-one oxalate After a mixture consisting of 7-hydroxy-3,4-dihyro-2H-1,4-benzothiazin-3-one (0.544 g, 3 mmol), 1-chloroacetyl-4-(2-quinolylmethyl)piperazine (0.911 g, 3 mmol), potassium carbonate (4.146 g, 30 mmol) and N,N-dimethylformamide (40 ml) was stirred for 1 day at room temperature under an argon gas stream, the solvent was distilled off under reduced pressure. Water was added to the residue, followed by extraction with chloroform. The extract was washed with water and then dried over anhydrous magnesium sulfate. The extract was subjected to chromatography on a silica gel column (developer: chloroform/methanol=50/1), whereby 0.786 g of the free base of the title compound was obtained as a yellow compound. Oxalic acid dihydrate (0.176 g, 1.4 mmol) was added to the oil (0.630 g, 1.4 mmol) and crystallization was then conducted from methanol, whereby 0.438 g of the title compound was obtained as pale yellow powder (yield: 58.1%).

m.p.: 184–186° C. (dec.)

$^1$H-NMR(CDCl$_3$)δ(ppm): 8.44–8.33(1H,m), 8.12–7.54 (6H,m), 6.97–6.75(2H,m), 4.83(2H,s), 4.49(2H,s), 3.97–3.80(4H,br), 3.40(2H,s), 3.33–3.17(4H,br).

IR(KBr)cm$^{-1}$: 1655, 1496, 1405, 1216, 720.

Example 99

Synthesis of 8-methyl-5-{1-[4-(2-quinolylmethyl) piperazinylcarbonyl]methoxy}-1,2,3,4-tetrahydroquinolin-2-one maleate In a similar manner as in Example 98, the title compound was obtained.

m.p.: 184–186° C. (dec.)

Example 100

Synthesis of 3,3,7-trimethyl-4-{1-[4-(2-quinolylmethyl) piperazinylcarbonyl]methoxy}-2,3-dihydro-1H-indol-2-one maleate In a similar manner as in Example 98, the title compound was obtained.

m.p.: 166–168° C. (dec.)

Example 101

Synthesis of 3,3,7-trimethyl-4-{3-[4-(2-quinolylcarbonyl) piperazinyl]propoxy}-2,3-dihydro-1H-indol-2-one maleate A mixture consisting of 4-(chloropropoxy)-3,3,7-trimethyl-2,3-dihydro-1H-indol-2-one (0.536 g, 2 mmol) and 1-(2-quinolylcarbonyl)piperazine (1.980 g, 8 mmol) was stirred for 4 hours at a bath temperature of 150° C. under an argon gas stream. The reaction mixture was allowed to cool down, and was then dissolved in chloroform. The solution was washed with water, dried over anhydrous magnesium sulfate, and then subjected to chromatography on a silica gel column (developer: chloroform/methanol=50/1) for purification, whereby 0.943 g of the free base of the title compound was obtained as a yellow oil (yield: 100%).

Maleic acid (0.232 g, 2 mmol) was added to the free base and crystallization was then conducted from ethanol, whereby 0.916 g of the title compound was obtained as white powder (yield: 77.8%).

m.p.: 176–178° C. (dec.)

$^1$H-NMR(DMSO-d$_6$)δ(ppm): 10.33(1H,s), 8.54(1H,d,J=8.3 Hz), 8.10–8.02(2H,m), 7.90–7.67(3H,m), 6.92(1H,d,J=9.3 Hz), 6.52(1H,d,J=9.3 Hz), 6.09(2H,s), 4.04(2H,t,J=5.9 Hz), 3.95–2.95(10H,br), 2.14(3H,s), 2.19–2.00(2H,br), 1.32 (6H,s).

IR(KBr)cm$^{-1}$: 1705, 1635, 1614, 1578, 1507, 1475, 1381, 1355, 1280, 1258, 1136, 1091, 982, 868, 766.

Example 102

Synthesis of 7-{3-[4-(2-quinolylcarbonyl)piperazinyl] propoxy}-3,4-dihydro-2H-1,4-benzothiazin-3-one maleate In a similar manner as in Example 101, the title compound was obtained.

m.p.: 173–175° C. (dec.)

Example 103

Synthesis of 8-methyl-5-{3-[4-(2-quinolyl-carbonyl) piperazinyl]propoxy}-1,2,3,4-tetrahydroquinolin-2-one maleate In a similar manner as in Example 101, the title compound was obtained.

m.p.: 182–184° C. (dec.)

Example 104

Synthesis of 7-{3-[4-(8-hydroxy-2-quinolylmethyl)-1-piperazinyl]propoxy}-3,4-dihydro-2H-1,4-benzothiazin-3-one dihydrochloride A 4N hydrogen chloride-ethyl acetate solution (0.45 ml) and a palladium-on-charcoal catalyst (90 mg) were added to a solution of 7-{3-[4-(8-benzyloxy-2-quinolylmethyl)-1-piperazinyl]propoxy}-3,4-dihydro-2H-1,4-benzothiazin-3-one (450 mg, 0.81 mmol) in acetic acid (6 ml), followed by stirring for 2 hours at a bath temperature of 80° C. under a hydrogen gas stream. The catalyst was filtered off from the reaction mixture and was then washed with methanol. The filtrate and the washing were mixed, followed by concentration under reduced pressure. The residue was purified by thin-layer silica gel chromatography while using chloroform/methanol(saturated with ammonia) (15/1) as an eluent, hereby 40 mg of the free base of the title compound were obtained in a pale yellow amorphous form. The catalyst was washed further with a saturated aqueous solution of sodium hydrogencarbonate and chloroform. The chloroform layer was dried over anhydrous sodium sulfate and then concentrated, whereby 108 mg of the free base of the title compound were obtained in the form of a pale yellow amorphous (39.3% in total).

This free base (148 mg) was dissolved in ethyl acetate (3 ml), followed by the addition of a 4N hydrogen chloride-ethyl acetate solution (0.18 ml) and ethanol (2 ml). The resulting mixture was stirred at room temperature for 1 hour. A precipitate was collected by filtration, whereby 168 mg of the title compound were obtained as pale brown powder (quantitative from the free base).

m.p.: 263–265° C. (dec.)

$^1$H-NMR(DMSO-$d_6$)δ(ppm): 10.41(1H,s), 8.46(1H,d,J= 8.5 Hz), 7.61(1H,d,J=8.5 Hz), 7.54–7.44(2H,m), 7.16(1H, dd,J=7.3,1.2 Hz), 6.93(1H,d,J=2.7 Hz), 6.90(1H,d,J=8.8 Hz), 6.80(1H,dd,J=8.8,2.7 Hz), 4.80(1H,br.s), 4.05(2H,t,J= 6.3 Hz), 3.73(2H,s), 3.42(2H,s), 2.52–2.49(10H,m), 2.23–2.14(2H,br).

IR(KBr)cm$^{-1}$: 1680, 1608, 1499, 1475, 1323, 1237.

Example 105
Synthesis of 7-{3-[4-(4-hydroxy-2-quinolylmethyl)-1-piperazinyl]propoxy}-3,4-dihydro-2H-1,4-benzothiazin-3-one In a similar manner as in Example 104, the title compound was obtained.

m.p.: 205–208° C. (dec.)

$^1$H-NMR(CDCl3-CD$_3$OD)δ(ppm): 8.29(1H,d,J=8.3 Hz), 7.64(1H,dd,J=7.8,7.1 Hz), 7.49(1H,d,J=7.8 Hz), 7.37(1H, m), 6.86–6.82(2H,m), 6.72(1H,m), 6.28(1H,s), 3.99(2H,t,J= 6.1 Hz), 3.57(2H,s), 3.38(2H,s), 2.75–2.49(10H,m), 1.98 (2H,br).

IR(KBr)cm$^{-1}$: 1672, 1632, 1606, 1496, 1473, 1233, 761.

Example 106
Synthesis of 2-hydroxy-7-{3-[4-(2-quinolylmethyl)-1-piperazinyl]propoxy}-3,4-dihydro-2H-1,4-benzothiazin-3-one 7-{3-[4-(2-quinolylmethyl)-1-piperazinyl]-propoxy}-3,4-dihydro-2H-1,4-benzothiazin-3-one-1-oxide (300 mg, 0.65 mmol) was dissolved in a mixed solvent consisting of 0.1 N hydrochloric acid (10 ml) and acetonitrile (10 ml), followed by stirring for 5 days at a bath temperature of 25° C. The reaction mixture was concentrated under reduced pressure, followed by the addition of water. The resulting mixture was washed with chloroform. The water layer was saturated with NaCl and then extracted with a 5:1 mixed solvent of chloroform and methanol. The extract was dried over anhydrous sodium sulfate and then concentrated under reduced pressure. The residue was subjected to chromatography on a silica gel column while using chloroform-methanol (10:1) as an eluent, whereby impurities which existed at the starting point were removed. Fractions containing the target compound were collected and then concentrated under reduced pressure. The concentrate was crystallized from chloroform-diethyl ether, whereby the 203 mg of the title compound were obtained as yellow powder (67.7%).

m.p.: 184–188

$^1$H-NMR(DMSO-$d_6$)δ(ppm): 8.00–7.92(2H,m), 7.73(1H, ddd,J=7.3,6.8,1.5 Hz), 7.64–7.54(2H,m), 6.96(1H,br.s), 6.92 (1H,d,J=8.8 Hz), 6.87(1H,d,J=2.4 Hz), 6.78(1H,dd,J=8.8, 2.4 Hz), 5.19(1H,s), 3.95(2H,t,J=6.2 Hz), 3.75(1H,s), 2.55–2.30(10H,cm,overlapped with solvent), 1.82(2H,t,J= 6.8 Hz).

IR(KBr)cm$^{-1}$: 2955, 2814, 1672, 1498, 1229, 1046.

Test 1
Antihistaminic Action and Anti-LTD$_4$ Action (In vitro Tests)

An isolated guinea pig ileum was cut into about 2 cm lengths. Each ileum piece was suspended in a 20-ml container filled with the Tyrode's buffer. An isotonic contractive response by histamine or LTD$_4$ was recorded on a recorder. The Tyrode's buffer was controlled at 30° C., through which a mixed gas (95%$O_2$-5%$CO_2$) was bubbled.

Antihistaminic action was determined by adding $10^{-3}$-$10^{-4}$ M histamine to an organ bath and measuring its dose-response. After the ileum piece was washed several times with the buffer, a test compound of a predetermined specific concentration was added. Sub-sequent to incubation for 30 minutes, the dose-response of histamine was measured again, and is presented in terms of p$A_2$ or p$D'_2$ at $10^{-5}$ M test compound in Table 11.

Antileukotrienic action was determined by investigating effects of addition of $10^{-5}$ M test compound on a contrative response caused by $10^{-8}$ M LTD$_4$, and is presented in terms of an inhibition rate at $10^{-5}$ M test in Table 11.

TABLE 11

| Example | Antihistaminic action (%) ($10^{-5}$ M) | Anti-LTD$_4$ action (%) ($10^{-5}$ M) |
|---|---|---|
| 1 | 8.22pA2 | 16 |
| 9 | 8.11pA2 | 40 |
| 26 | 8.01pD's | 27 |
| 29 | 8.79pA2 | 48 |
| 32 | 8.64pA2 | 20 |
| 36 | 9.12pA2 | 46 |
| 39 | 9.08pA2 | 30 |
| 42 | 9.33pA2 | 13 |
| 44 | 8.67pA2 | 47 |
| 61 | 8.47pA2 | 19 |
| 69 | 9.42pA2 | 25 |
| 78 | 8.37pA2 | 27 |
| 79 | 8.48pA2 | 19 |
| 80 | 9.15pA2 | 11 |
| 81 | 8.04pA2 | 19 |
| 83 | 9.37pA2 | 26 |
| 85 | 8.55pA2 | 21 |
| 88 | 8.67pA2 | 12 |
| 89 | 8.55pA2 | 21 |
| 90 | 10.06pA2 | 16 |
| 92 | 8.22pA2 | 42 |
| 102 | 8.69pA2 | 10 |
| Terfenadine | 8.24pA2 | — |

Tests 2
H$_1$ Receptor Binding Inhibition Test

Incubated at 37° C. for 30 minutes was 1 ml of a 50 mM phosphate buffer (pH 7.5) which contained 0.3 nM [$^3$H] mepyramin (activity: 22 Ci/mmol), guinea pig cerebromembranous protein and a test compound. An ice-cold phosphate buffer was added to terminate the reaction, followed by immediate filtration through a Wattman CF/C filter. The filter was washed twice with 20 ml aliquots of the ice-cold buffer. The radio-activity of the residue was measured by a liquid scintillation counter. From a measurement value obtained without the addition of the test compound and measurements values obtained upon addition of the test compound at various concentrations, the dose-response of the inhibitory action of the test compound was measured and the 50% inhibitory concentration ($IC_{50}$) was determined. Using the Cheng-Prusoff formula, a dissociation constant ($K_D$) was calculated from the 50% inhibitory concentration ($IC_{50}$).

In a binding assay, $10^4$M R(-)dimethindene was used for the measurement of a nonspecific binding. From the binding assay, it was found that the receptor was of only one type and that the maximum binding (Bmax) was 278±24 fmol/mg protein. Further, the dissociation constant ($K_D$) of [$^3$H] mepyramin was $3.30±0.26×10^{-9}$ M and when analyzed by a Hill plot, its slope was found to be 1.005.

Test 3
$LTD_4$ Receptor Binding Inhibition Test

Incubated at 22° C. for 30 minutes was 0.3 ml of a 10 mM piperazine N,N'-bis(2-ethanesulfonate) buffer (pH 7.5) which contained 0.2 nM [$^3$H]$LTD_4$, guinea pig pulmomembranous protein and a test compound. An ice-cold tris hydrochloride/sodium chloride buffer (10 mM/100 mM, pH 7.5) was added to terminate the reaction, followed by immediate filtration through a Wattman CF/C filter. The filter was washed twice with 20 ml aliquots of the ice-cold buffer. The radioactivity of the residue was measured by a liquid scintillation counter. By similar methods as in the $H_1$ receptor test, the $IC_{50}$ of the test compound was determined and the dissociation constant ($K_D$) was calculated as presented in Table 12.

In a binding assay, 2 pM $LTD_4$ was used for the measurement of a nonspecific binding. From the binding assay, it was found that the receptor was of only one type and that the maximum binding (Bmax) was 988 fmol/mg protein. Further, the dissociation constant ($K_D$) of [$^3$H]$LTD_4$ was $2.16×10^{-10}$M and when analyzed by a Hill plot, its slope was found to be 0.99.

TABLE 12

| Example | H1 receptor (%) | LTD4 receptor (%) |
|---|---|---|
| 1 | $1.73 × 10^{-7}$ | $3.24 × 10^{-6}$ |
| 9 | $1.35 × 10^{-8}$ | $4.96 × 10^{-5}$ |
| 26 | $3.63 × 10^{-8}$ | $3.34 × 10^{-6}$ |
| 36 | $3.49 × 10^{-12}$ | $1.99 × 10^{-6}$ |
| 41 | $4.32 × 10^{-9}$ | $3.83 × 10^{-6}$ |
| 45 | $3.39 × 10^{-9}$ | $1.98 × 10^{-6}$ |
| 50 | $4.57 × 10^{-7}$ | $8.60 × 10^{-6}$ |
| 54 | $2.49 × 10^{-10}$ | $8.81 × 10^{-4}$ |
| 60 | $5.45 × 10^{-9}$ | $8.73 × 10^{-6}$ |
| 61 | $4.69 × 10^{-9}$ | $1.61 × 10^{-6}$ |
| 75 | $5.58 × 10^{-8}$ | $7.34 × 10^{-6}$ |
| 77 | $7.45 × 10^{-8}$ | $1.10 × 10^{-4}$ |
| 78 | $1.82 × 10^{-8}$ | $7.43 × 10^{-6}$ |
| 79 | $7.59 × 10^{-8}$ | $8.61 × 10^{-6}$ |
| 80 | $4.31 × 10^{-9}$ | $1.84 × 10^{-5}$ |
| 85 | $1.83 × 10^{-8}$ | $3.57 × 10^{-5}$ |
| 90 | $5.01 × 10^{-9}$ | $9.41 × 10^{-6}$ |
| 92 | $5.57 × 10^{-8}$ | $4.23 × 10^{-6}$ |
| 93 | $7.10 × 10^{-8}$ | $5.90 × 10^{-6}$ |
| 97 | $1.87 × 10^{-7}$ | $1.59 × 10^{-5}$ |
| Telfenadine | $1.52 × 10^{-7}$ | — |

Test 4
Brain Penetration Test

A brain penetration test was conducted based on the method proposed by Zang, M. Q. (J. Med. Chem., 38, 2472–2477, 1995). Described specifically, to a mouse of 20 g to 23 g, a test compound of a given concentration was peritoneally administered. Upon elapsed time of one hour after the administration, the mouse was sacrificed. The brain tissue was taken out, and was then homogenated with a 30 mM Na,K phosphate buffer (pH 7.5) to give 40 ml/g wet weight. The homogenate was divided into three test tubes (900 μl), followed by the addition of 100 μl of [$^3$H] mepyramin solution (final concentration: 0.5 nM). Subsequent to incubation at 37° C. for 50 minutes, an ice-cold phosphate buffer was added to terminate the reaction. Each of the resulting mixtures was immediately filtered through Wattman CF/C filter. The filter was washed twice with 20 ml aliquots of the ice-cold buffer. The radioactivity of the residue was measured by a liquid scintillation counter. From a measurement value obtained without administration of the test compound and measurement values obtained when the test compound were administered at respective doses, the dose-response of the inhibitory reaction by the test compound was measured to determine its 50% inhibitory dose ($IC_{50}$). A BP index as an index of brain penetration was calculated in accordance with the following formula:

BP index=$IC_{50}$ (mg/kg)/$H_1$ binding inhibition dissociation constant (nM)

TABLE 13

| Compound | $IC_{50}$ (mg/Kg, ex vivo) | BP index |
|---|---|---|
| Ex. 90 | 8.5 | 1.7 |
| Ex. 91 | 10 | 35.7 |
| Ex. 92 | 16.5 | 0.29 |
| Telfenadine | 26 | 0.17 |

Capability of Exploitation in Industry

The diamine derivatives (1) or salts thereof according to the present invention have antileukotrienic action and antihistaminic action in combination and are low in brain penetration, are hence useful as medicines such as asthma preventives and curatives.

What is claimed is:

1. A compound represented by the following formula or a salt, solvate or isomer thereof:

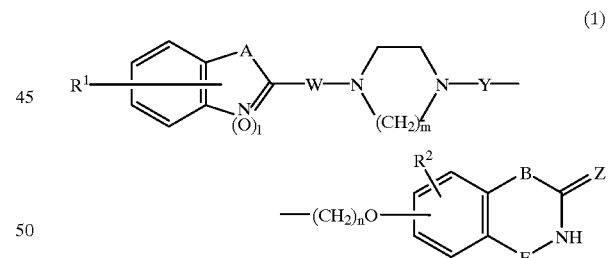

wherein
$R^1$ is selected from the group consisting of a hydrogen atom, a hydroxyl group, an aralkyloxy group and a halogen atom, $R^2$ is selected from the group consisting of a hydrogen atom and a lower alkyl group, A is selected from the group consisting of —O—, —S—, —CH=CH—, —COH=CH—, —CH=N—, and —N—($R^4$), wherein $R^4$ is a lower alkyl group or an alkoxyalkyl group, B is selected from the group consisting of a single bond, —CH=CH—, —S(O)$_q$CH$_2$—, —S(O)$_q$CHOH—, CHOH—, and —C($R^5$)($R^6$)—(CH$_2$)$_k$—, wherein $R^5$ and $R^6$ are the same or different and are either a hydrogen atom or a lower alkyl group, q is a value of 0 to 2, and k is a value of 0 to 2, E is selected from the group consisting of a single bond and —$(CH_2)_3$—, W is selected from the group consisting of —$CH_2$— and —CO—, Y is selected from the group consisting of —$CH_2$— and —CO—, Z is selected from the group consisting of O and S, and (l) is a value of either 0 or 1, m is a value of either 2 or 3, and n is a value of 1 to 4;

wherein when E is "—$(CH_2)_3$—" then B is a single bond, and when E is a single bond, then B is a group other than a single bond.

2. A composition comprising a compound of claim 1 and a pharmaceutically acceptable carrier.

3. A method for providing an antihistaminic response comprising administering an effective amount of a compound of claim 1.

4. A method for providing an antileukotrienic response comprising administering an effective amount of a compound of claim 1.

5. A method of treating an inflammatory or allergic disease mediated by leukotrienes or by histamines comprising administration of an effective amount of a compound of claim 1 to a subject in need of treatment.

6. A method of treating allergy or rhinitis comprising administering an effective amount of the compound of claim 1 to a subject in need of treatment.

7. A method of treating asthma comprising administering an effective amount of the compound of claim 1 to a subject in need of treatment.

* * * * *

UNITED STATES PATENT AND TRADEMARK OFFICE
CERTIFICATE OF CORRECTION

PATENT NO.   : 6,127,360
DATED        : October 3, 2000
INVENTOR(S)  : Henk Timmerman, et al.

It is certified that error appears in the above-identified patent and that said Letters Patent is hereby corrected as shown below:

Title page, Item [75],
The 2nd Inventor's name and Residence are listed incorrectly. Item [75] should read as follows:

[75] Inventors: Henk Timmerman, Voorschoten, Netherlands; Mingqiang Zang, Edinburgh, Scotland, United Kingdom; Kazuhiro Onogi, Iruma, Japan; Masahiro Tamura; Tsutomu Tohma, both of Higashimurayama, Japan; Yasushi Wada, Tachikawa, Japan Signed and Sealed this Third Day of July, 2001

*Attest:*

NICHOLAS P. GODICI
*Attesting Officer*  *Acting Director of the United States Patent and Trademark Office*